US010242127B2

(12) United States Patent
De Stavola et al.

(10) Patent No.: US 10,242,127 B2
(45) Date of Patent: Mar. 26, 2019

(54) METHOD FOR MAKING A SURGICAL GUIDE FOR BONE HARVESTING

(71) Applicant: Nobel Biocare Services AG, Kloten (CH)

(72) Inventors: Luca De Stavola, Selvazzano Dentro (IT); Andrea Fincato, Campo San Martino (IT)

(73) Assignee: NOBEL BIOCARE SERVICES AG, Kloten (CH)

( * ) Notice: Subject to any disclaimer, the term of this patent is extended or adjusted under 35 U.S.C. 154(b) by 413 days.

(21) Appl. No.: 14/892,840

(22) PCT Filed: May 22, 2014

(86) PCT No.: PCT/IB2014/061624
§ 371 (c)(1),
(2) Date: Nov. 20, 2015

(87) PCT Pub. No.: WO2014/188369
PCT Pub. Date: Nov. 27, 2014

(65) Prior Publication Data
US 2016/0106513 A1 Apr. 21, 2016

(30) Foreign Application Priority Data
May 22, 2013 (IT) .............................. MI2013A0831

(51) Int. Cl.
*G06T 7/00* (2017.01)
*G06F 17/50* (2006.01)
(Continued)

(52) U.S. Cl.
CPC .............. *G06F 17/50* (2013.01); *A61B 17/15* (2013.01); *A61B 17/152* (2013.01); *A61B 34/10* (2016.02);
(Continued)

(58) Field of Classification Search
CPC ..... G06F 19/3481; G06F 17/50; A61B 34/10; A61B 34/20; A61B 34/108;
(Continued)

(56) References Cited

U.S. PATENT DOCUMENTS

2007/0288030 A1* 12/2007 Metzger ............... A61B 17/154
606/87
2010/0152782 A1* 6/2010 Stone .................. A61B 17/151
606/280
2012/0123423 A1 5/2012 Fryman

FOREIGN PATENT DOCUMENTS

EP 2179701 A1 4/2010

OTHER PUBLICATIONS

International Search Report in PCT/IB2014/061624, dated Oct. 23, 2014.

* cited by examiner

Primary Examiner — Caridad Everhart
(74) Attorney, Agent, or Firm — Knobbe Martens Olson & Bear LLP

(57) ABSTRACT

A method for making a surgical guide for bone harvesting identifying in a three-dimensional image of a bone one or more sensitive anatomic structures and a volume of bone suitable for being removed. The volume is delimited by a portion of an outer surface of the bone defining a perimeter and by a mantle extending from the perimeter inside of the bone. The method also includes designing the surgical guide which includes defining a guide surface including a work area delimited by guide walls. The method also includes angling at least one of the guide walls so that the guide wall includes a face that constitutes a geometrical extension of a portion of the mantle when the guide is rested on the outer
(Continued)

surface of the bone such that the face includes at least one segment forming a predetermined angle with respect to the guide surface.

16 Claims, 15 Drawing Sheets

(51) Int. Cl.
| | | |
|---|---|---|
| | *G06F 7/60* | (2006.01) |
| | *A61B 17/15* | (2006.01) |
| | *G06T 7/62* | (2017.01) |
| | *A61B 17/16* | (2006.01) |
| | *A61B 17/17* | (2006.01) |
| | *A61B 17/00* | (2006.01) |
| | *A61B 17/56* | (2006.01) |
| | *A61B 90/00* | (2016.01) |
| | *A61B 34/10* | (2016.01) |

(52) U.S. Cl.
CPC .............. *G06T 7/0012* (2013.01); *G06T 7/62* (2017.01); *A61B 17/1635* (2013.01); *A61B 17/176* (2013.01); *A61B 2017/00526* (2013.01); *A61B 2017/568* (2013.01); *A61B 2034/108* (2016.02); *A61B 2090/034* (2016.02); *G06T 2207/10012* (2013.01); *G06T 2207/30008* (2013.01)

(58) Field of Classification Search
CPC ........ A61B 2034/108; A61B 2034/107; A61B 17/15; A61B 17/152; A61B 17/176; A61B 17/157; A61B 17/1635; G06T 7/0012; G06T 7/62
See application file for complete search history.

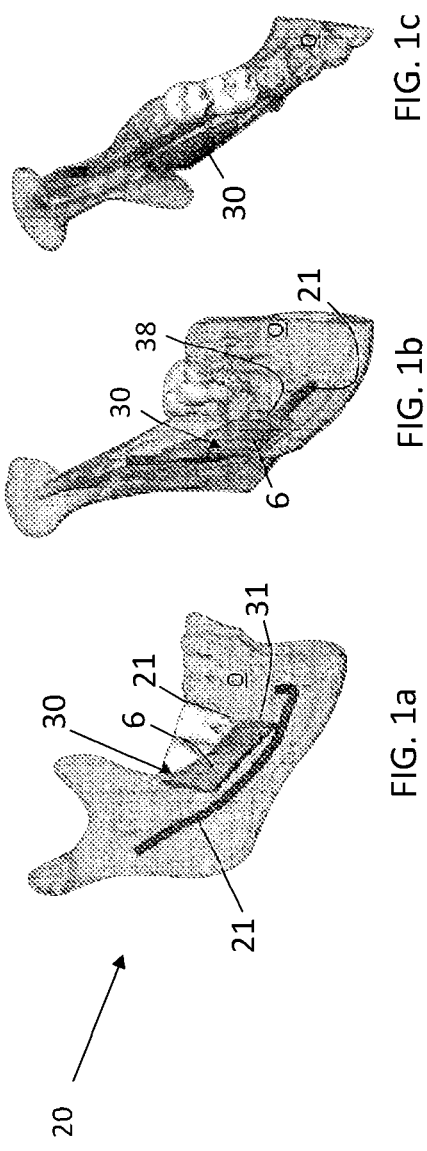
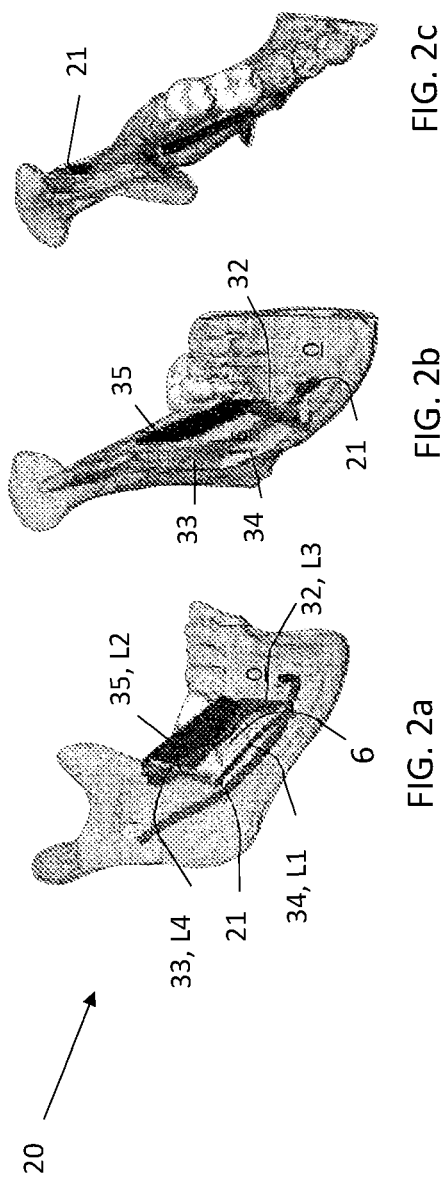

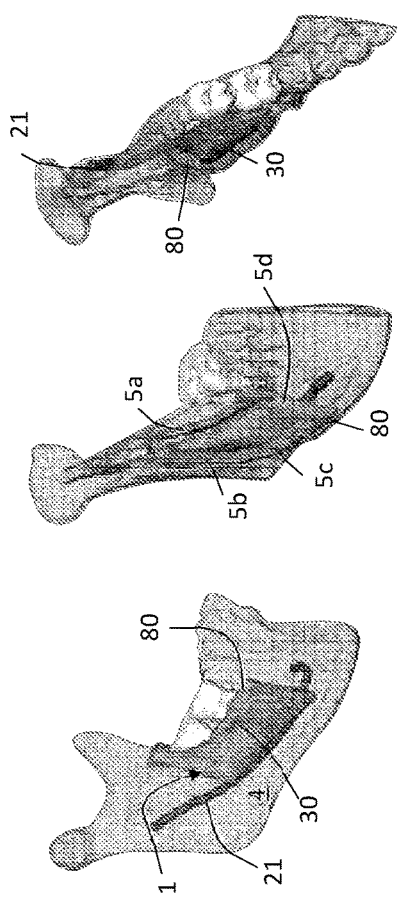
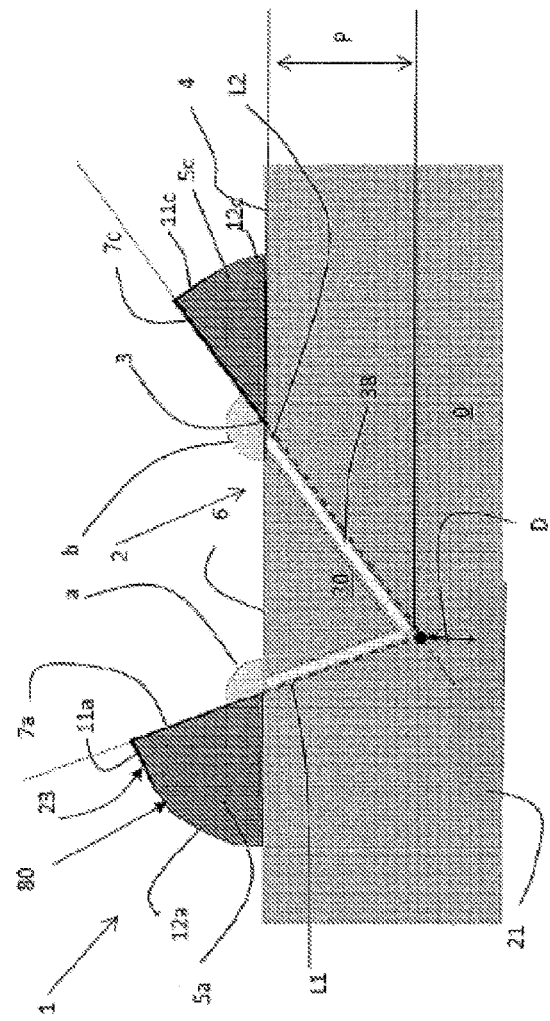

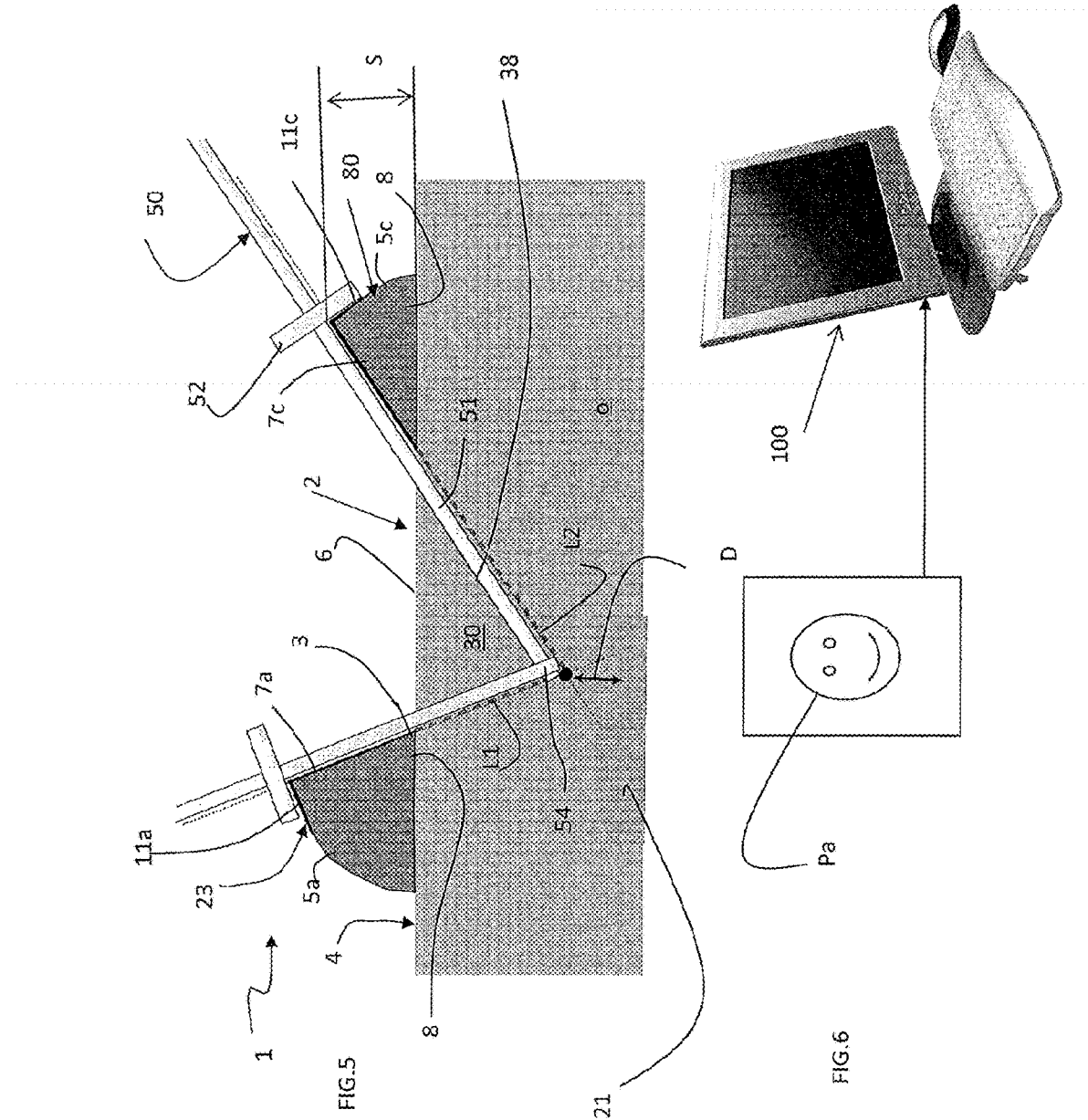

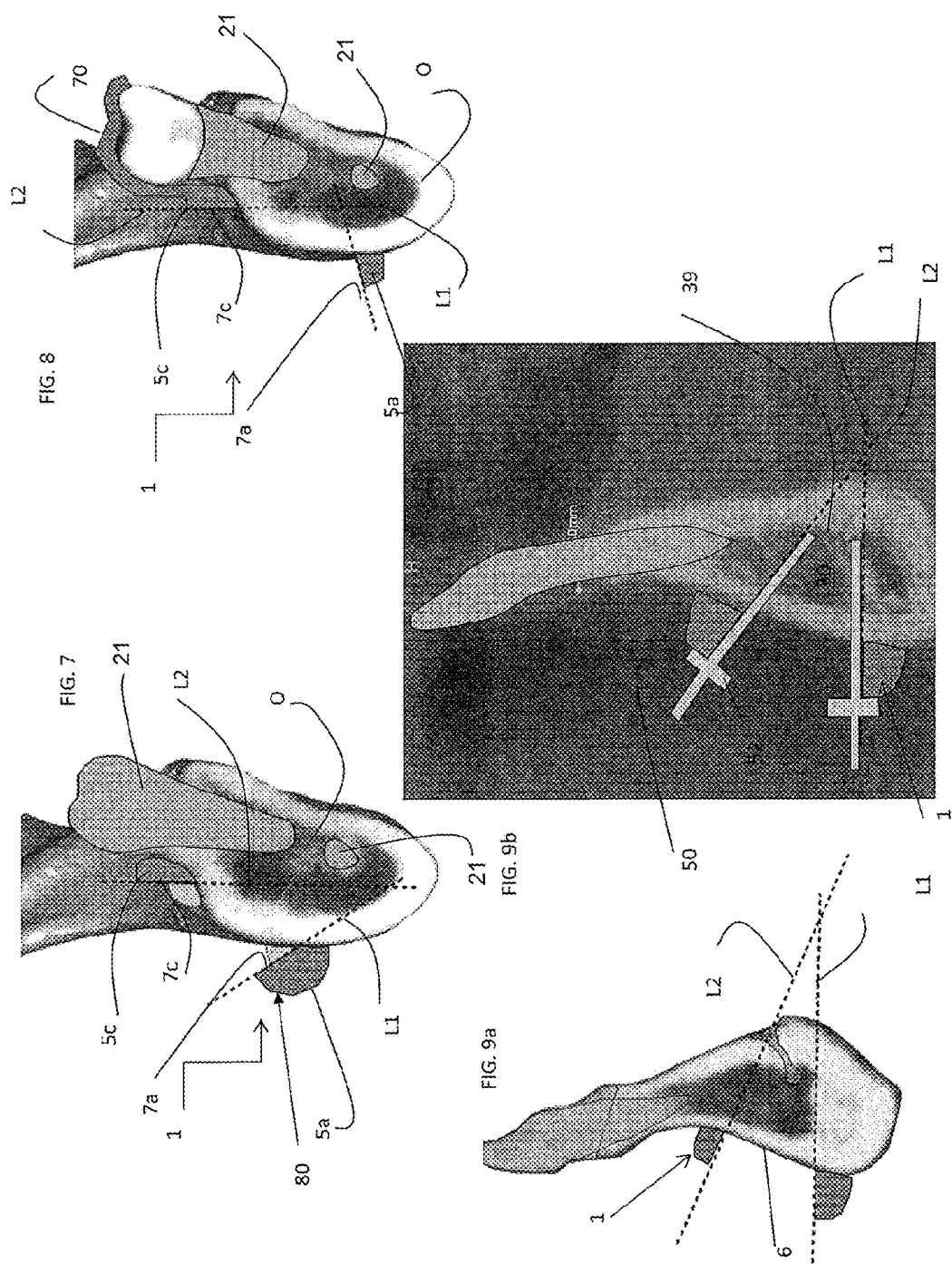

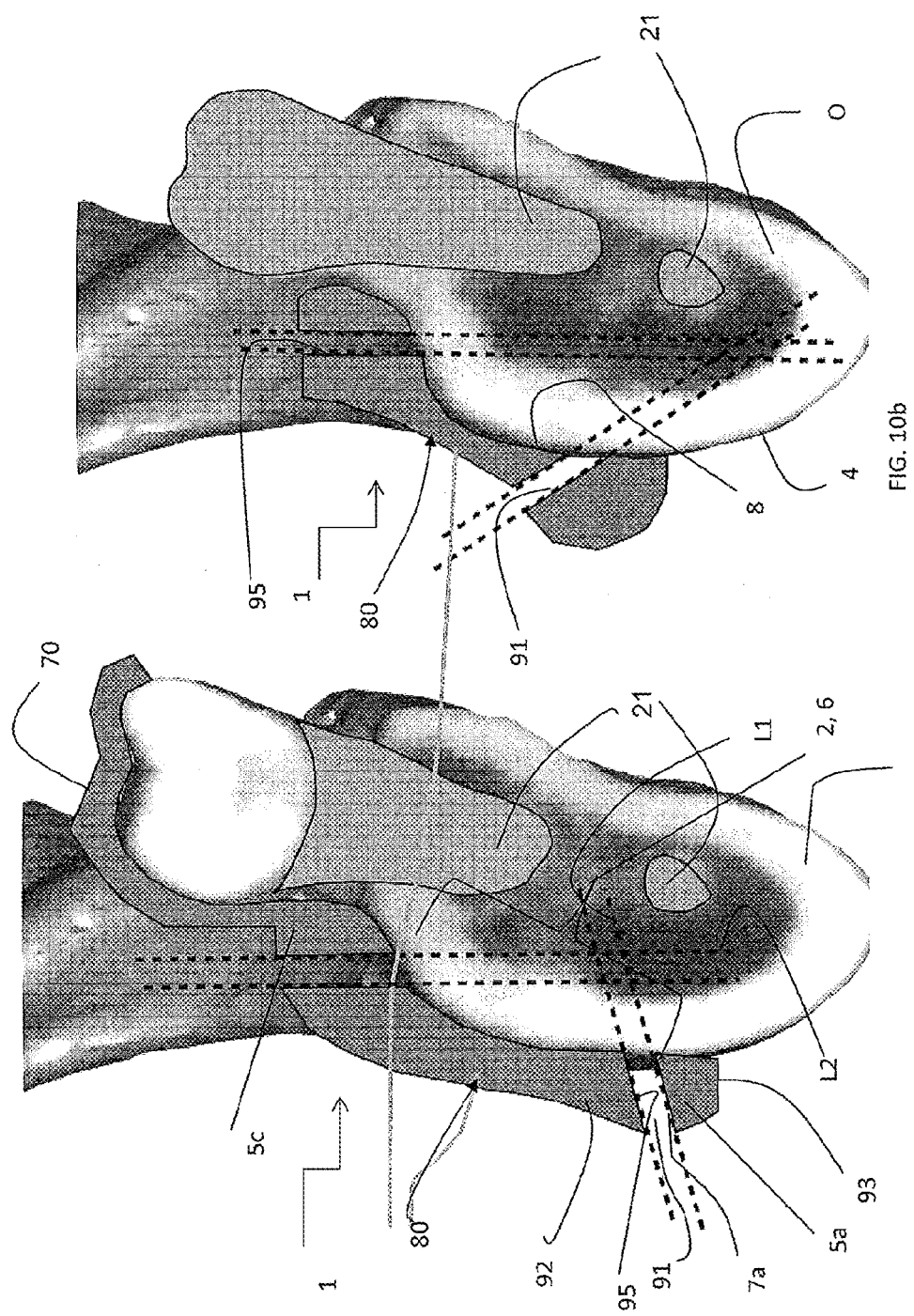

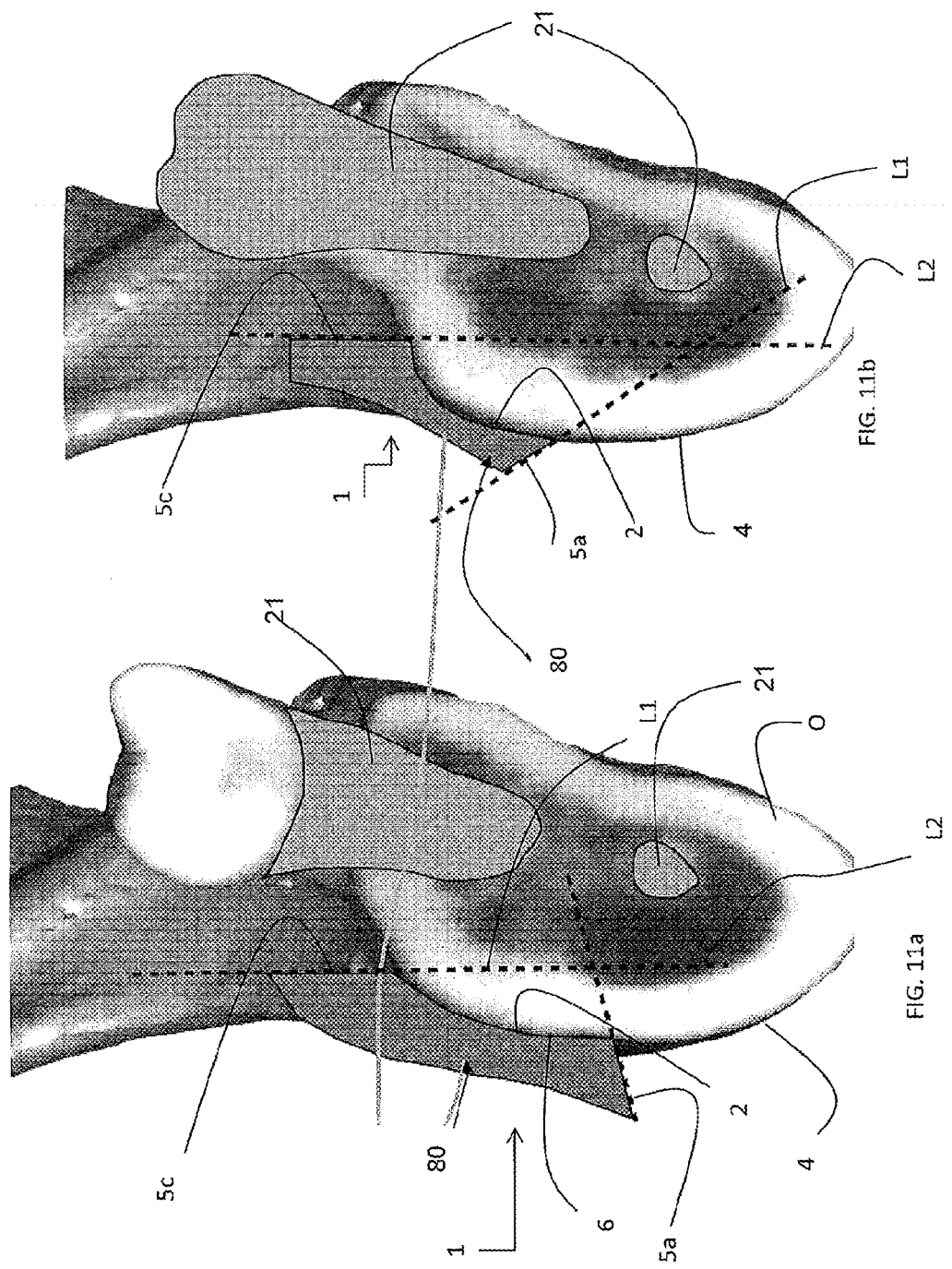

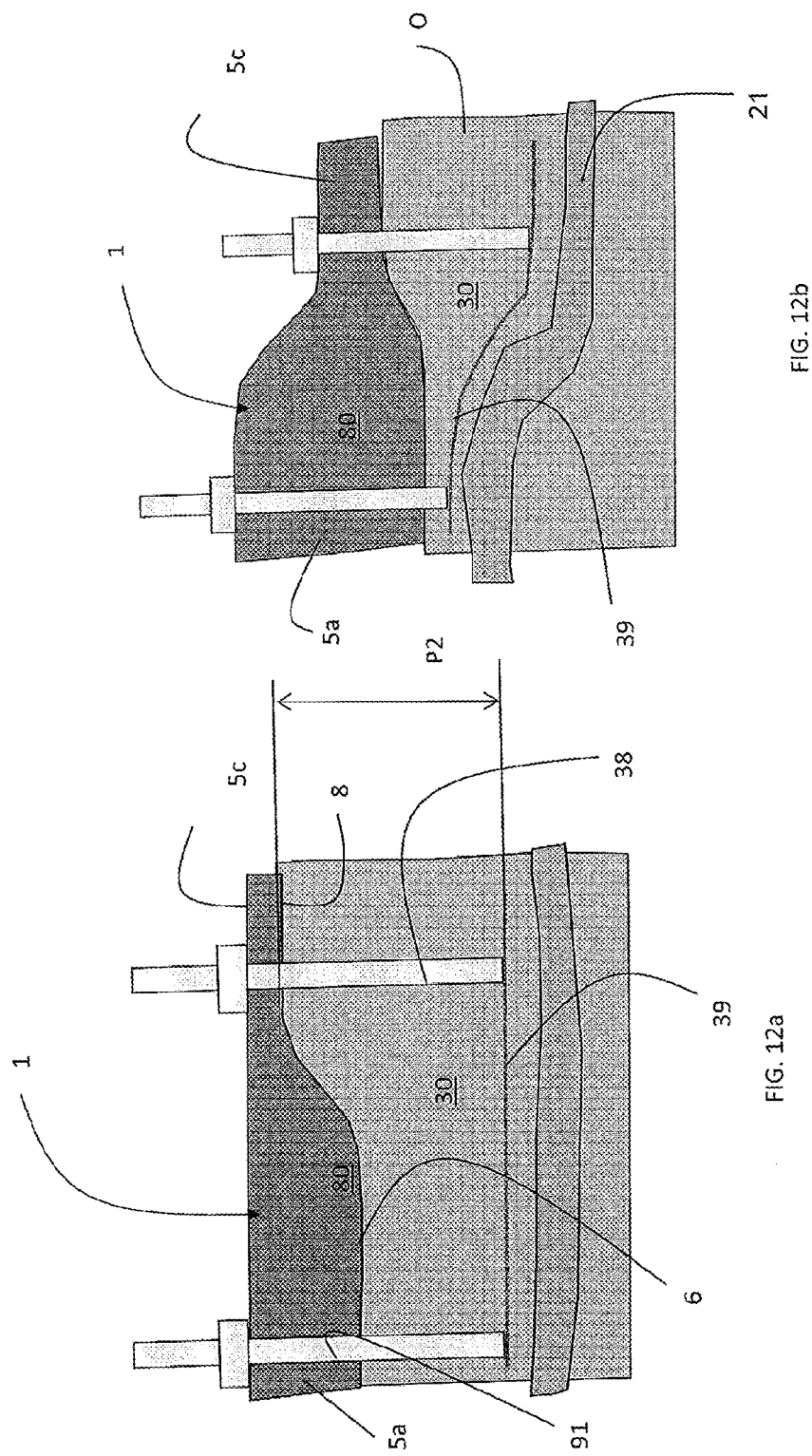

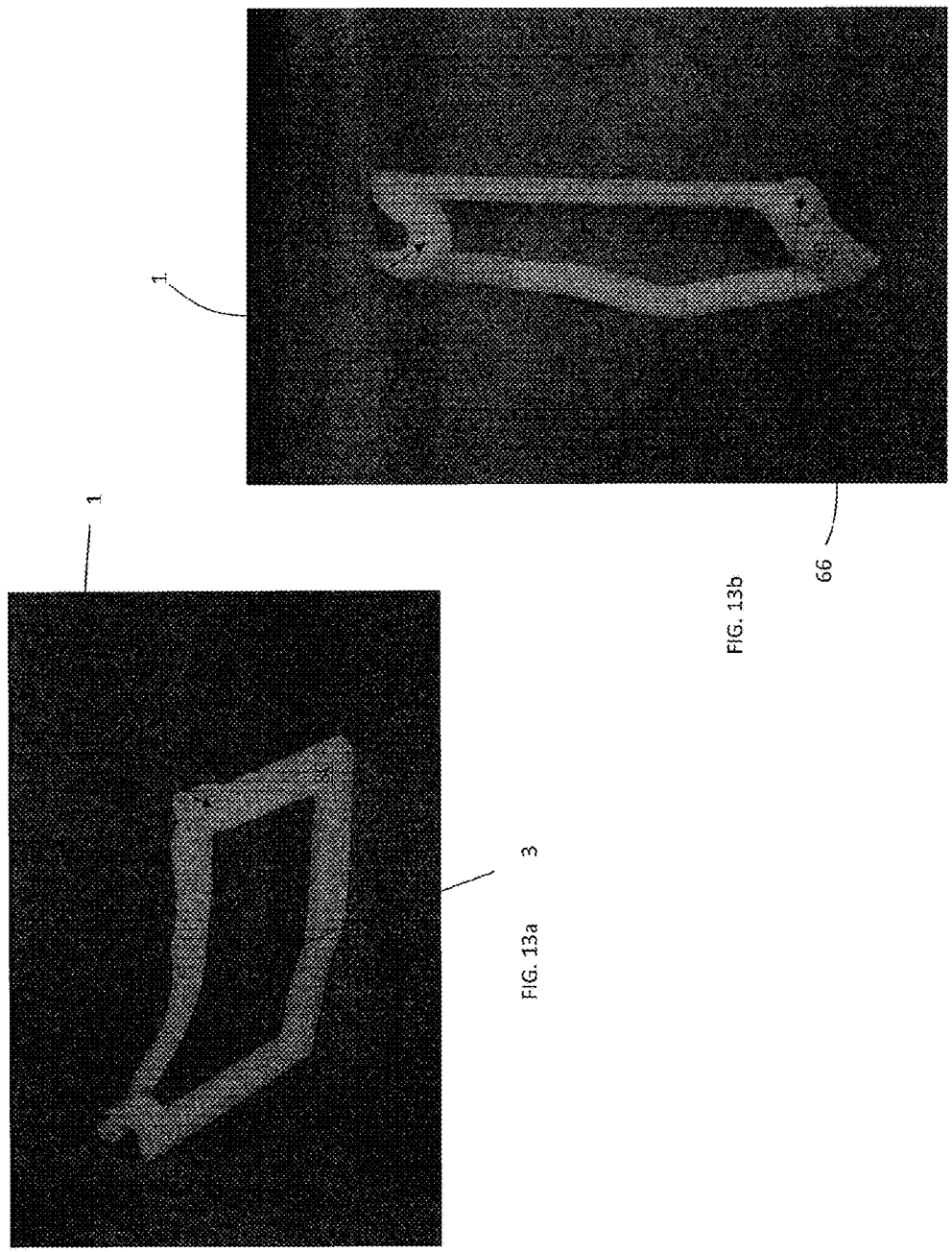

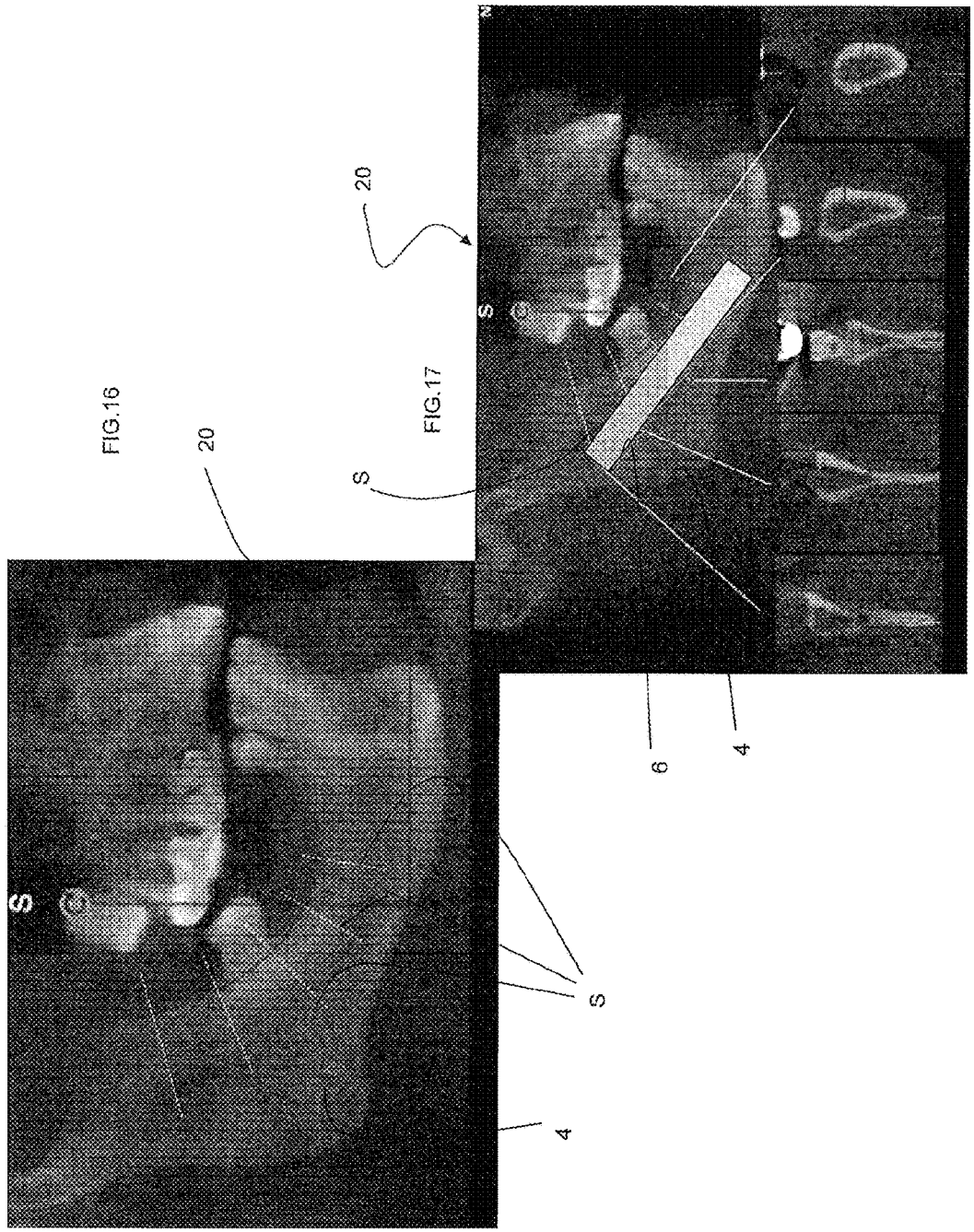

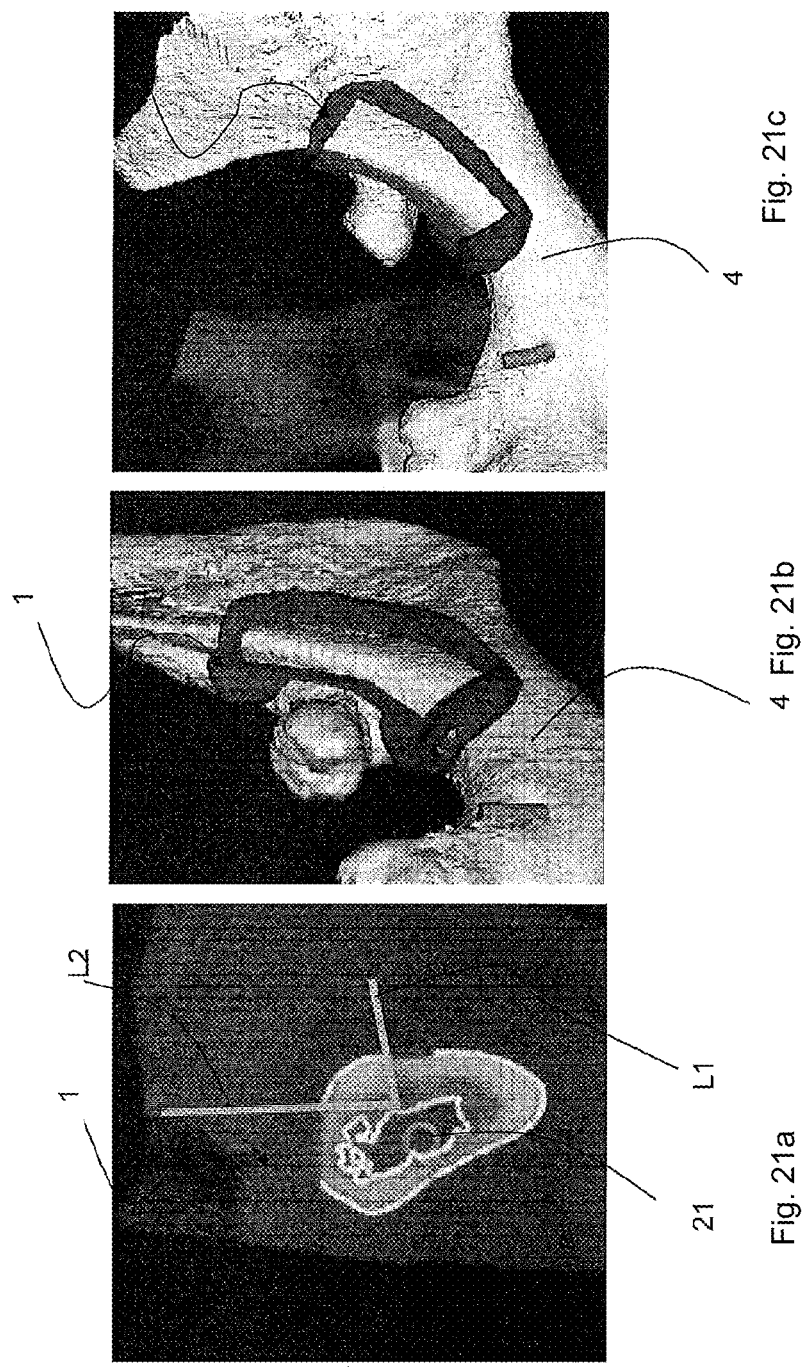

METHOD FOR MAKING A SURGICAL GUIDE FOR BONE HARVESTING

CROSS-REFERENCE TO RELATED APPLICATIONS

This application is a 371 National phase filing of PCT/IB2014/061624 with an International Filing Date of May 22, 2014, which claims the benefit of Italian Application No. MI2013A000831, which was filed on May 22, 2013, and which are incorporated herein by reference in their entirety.

FIELD OF INVENTION

The present invention relates to a method for making a surgical guide for performing bone incisions to be used in bone harvesting procedures. The surgical guide accurately provides the surgeon or medical professional with the working parameters with respect to the resting bone surface where the guide is positioned, and its configuration depends on the evaluation of the specific anatomy of the patient, reconstructed through a three-dimensional survey, thus allowing all the bone incisions to be performed while respecting sensitive anatomic structures (for example, neuro-vascular and dental structures).

BACKGROUND

The present invention concerns the field of surgery and in particular the field of autologous bone harvesting for reconstructing bone defects. Preferably, but not exclusively, the invention applies to the field of oral surgery.

After a dental element has been lost (due to trauma or pathology) the alveolar ridge generally undergoes restructuring that always ends up with a reduction of its original volume. Such a reduction very often determines the lack of adequate bone structure for the correct three-dimensional insertion of a dental implant. There are various reconstruction techniques of atrophic alveolar ridges. The material considered "gold standard" for such surgery is autologous bone, i.e. harvesting of a bone element from the patient himself so that it can be autografted in the atrophic area.

The body of the mandible has an outer face, an inner face, a lower margin or base and a rear face. The outer face has the chin symphysis in the middle, which is the midpoint of the join of the two separate primitive outlines of the bone and ends at the bottom with the mental protuberance. In this same face it is possible to see, at the level of the 2nd premolar tooth, the lateral mental foramen, the opening of the channel of the mandible; at the level of the 2nd and 3rd molar tooth there is an oblique ridge, the buccinator groove, on which the homonymous is located. The upper end of the buccinator groove marks the boundary between body and ramus. The side lip of the groove becomes more substantial and represents the outer oblique line of the mandible.

The locations generally preferred for intra-oral harvesting are the outer oblique line and the mental symphysis. The limits and the risks of such a procedure are described in the literature and include:
- risk of lesion of the lower alveolar nerve;
- risk of lesion of the mental nerve close to the homonymous foramen;
- risk of lesion of the dental neuro-vascular tissue;
- risk of mandible fracture;
- risk of lesion of the dental roots;
- volumetric limit with regard to the bone defect to be treated, i.e. limit to the amount and size of bone that it is possible to harvest.

Such risks are determined by the fact that it is impossible to clinically translate the detailed information obtained from radiograph examinations, TAC or other that allow a three-dimensional reconstruction of the anatomy of the patient. In other words, it is very complex, even if a detailed analysis of the anatomy of the patient has been carried out through three-dimensional imaging techniques, to make what has been analysed in the three-dimensional reconstructions of the anatomy correspond with the actual arrangement of the anatomical structure of the patient "live" due to the lack of real reference points between the visible external anatomical structure and the inner one.

In the anatomical area of the external oblique line, the risk areas are:
- rear limit to the anatomical boundary with the area of the mandibular ramus where it is extremely complex to determine "with the naked eye" the profile and the depth of the alveolar channel (lower alveolar nerve);
- medial or internal limit where it is extremely complex to determine "with the naked eye" the profile of the roots of the teeth present and/or of the lingual bone theca;
- front limit where it is extremely complex to determine "with the naked eye" the profile of the alveolar nerve close to the mental foramen;
- more generally, it is extremely complex to determine "with the naked eye" an accurate control of the work axis of the bone cutting tools, be they rotary or piezoelectric tools.

In the area of the mental symphysis the risk areas are:
- lower limit where it is extremely complex to precisely determine "with the naked eye" the lower edge of the mandible (presence of the mental muscle whose uppermost attachment must be respected);
- upper limit where it is extremely complex to determine "with the naked eye" the profile of the roots of the front teeth;
- rear limit where it is extremely complex to determine "with the naked eye" the profile of the loop of the lower alveolar nerve and of that of the incisor;
- more generally, also in this case it is extremely complex to determine "with the naked eye" an accurate control of the work axis of the bone cutting tools, be they rotary or piezoelectric tools.

The fact that it is not possible to work with accuracy and certainty means an approximation in performing the surgical procedure, reduction of the bone volumes harvested and increased risks of the surgery.

SUMMARY OF THE INVENTION

The present invention relates to a method for making a surgical guide suitable for solving all of the problems encountered according to the prior art. In particular, said guide is suitable for giving the operator a correct reference point for performing an osteotomy in maximum safety and with the desired results.

It is known that while an osteotomy is being performed, in particular for an autologous transplant, it is desirable to have optimal control of the dimensions of bone volume harvested, these dimensions depending on the amount of bone necessary to reconstruct the portion of bone damaged. However, at the same time the harvesting must take place in the greatest possible safety without harming sensitive anatomic structures of the patient. In other words, in harvesting, the nerves, blood vessels, muscles, tendons, dental roots, etc.

belonging to the patient must not suffer damages. The guide made according to the method of the invention has the main purpose of being suitable for improving an osteotomy of known and specified dimensions and at the same time to protect as much as possible to anatomical structures of the patient. Such an osteotomy can be carried out in any point of the patient's skeleton, with preference for the mandible area.

The guide made according to the method of the invention is also completely dependent on the anatomy of the patient, i.e. it is made on a specific patient, and cannot be substantially used for another patient.

According to one aspect, the invention relates to a method for designing a surgical guide for performing bone harvesting, including:

Providing a three-dimensional image of at least one portion of the bone of a patient where said harvesting is to be performed, said bone defining an outer surface;

Identifying in said three-dimensional image one or more sensitive anatomic structures that must not be involved in said bone harvesting;

Identifying in said three-dimensional image a volume of bone suitable for being removed in said bone harvesting, said volume excluding said sensitive anatomic structures, and said volume being delimited by a portion of said outer surface of said bone defining a perimeter and by a mantle extending from said perimeter inside said bone, said mantle including, for each point of said perimeter, a segment forming a predetermined angle with said portion of outer surface, said angle corresponding to a cutting direction inside said bone identified in said three-dimensional image;

establishing the parameters of said surgical guide, said step including:

defining a guide surface suitable for facing said outer surface of said bone, said guide surface comprising a work area delimited by guide walls;

Angling at least one of said walls with respect to said guide surface, so that said wall includes a face that constitutes a geometrical extension of a portion of said mantle of said bone volume, when said guide faces said outer surface portion of bone, so that said face includes a segment forming a predetermined angle with respect to said guide surface.

With the method of the invention, therefore, a surgical guide is made based on a three-dimensional image of the portion of bone of the patient where the harvesting must be performed.

The three-dimensional image can be obtained by the same operator, so that in this case providing the three-dimensional image includes generating or making the three-dimensional image, or the three-dimensional image is imported from a memory support or by online downloading in a known way. Making the guide can be purely virtual, i.e. the designing of the guide can comprise just making a file including the physical parameters for making the guide itself. The guide is made so as to include a work area having a perimeter such that, when a suitable cutting tool is used, it is rested on the guide walls and guided along the perimeter of the work area, so as to be substantially guided to cut the bone at the perimeter of the bone surface to be cut and to penetrate inside the bone at the mantle of the volume of bone to be removed. In other words, the cutting tool is guided by the guide walls to enter into the bone with an angle corresponding to the angle formed by the outer mantle of the volume of bone to be removed with the outer surface of the bone.

For example, in the case in which the guide is rested on the outer surface of the bone, the perimeter of the work area corresponds to a perimeter of the bone surface to be cut in the bone harvesting.

In other words, the bone volume to be removed is delimited by a portion of outer surface of the bone and by a mantle. The guide is associated with, i.e. faces, the outer surface of bone, in other words the guide can either rest in contact with the bone itself, or can be raised with respect to the bone, for example anchored to teeth or other support elements. The direction inside the bone of the bone volume to be removed is defined by the mantle that extends inside the bone from the perimeter of the portion of outer surface of bone. The mantle includes that which is geometrically called a "ruled surface", in other words it includes a portion of a surface formed from a plurality of straight lines. In fact, the mantle, which extends from the perimeter of the outer surface portion of bone to be removed towards the inside of the bone, preferably for each point of such a perimeter includes a segment that starts from a point of the perimeter and extends towards the inside of the bone, forming a certain angle with respect to the bone surface. This angle is established by the surgeon or operator according to the method of the invention so as to avoid the sensitive anatomic structures as well as to obtain a sufficiently thick bone volume.

The bone volume in addition to the mantle and to the portion of outer surface of bone from which the mantle extends, can include a portion of bottom surface, i.e. the mantle can connect two distinct portions of inner and outer surface of bone. Alternatively, the mantle can close on itself in the case in which the generator lines thereof converge in a single point or line to form a conoid with the portion of outer surface of bone as base.

The angling of the mantle, i.e. the angling of each segment forming the mantle with respect to the bone surface, is set in the design of the guide, i.e. thanks to the angling of a face arranged in one of the walls of the guide, the direction of the cut inside the bone from the outer surface thereof is determined, since the cutting tool rests on such a face during the cutting of the bone.

In other words, the geometry of the volume of bone to be removed is set in the guide. The guide is designed so as to have a work area that has an extension that allows the work tool to go around the perimeter of the outer surface of bone to be removed.

The work area of the guide has a perimeter corresponding to the perimeter of the surface portion of bone of the volume of bone to be removed in the case in which it is rested on the bone, or less or more than this depending on the angling of the faces of the guide.

In a preferred example, the perimeter of the portion of surface of bone and the perimeter of the work area coincide, i.e. they are juxtaposed. This situation happens when the guide is rested on the outer surface of the bone. In a further preferred example, the perimeter of the work area is larger or smaller than the perimeter of the outer surface portion of the volume of bone to be removed according to the angling of the faces. This situation happens when the guide is spaced from the outer bone surface. The work area and the outer surface of bone are two sections of the solid generated by the straight lines that define the mantle of the volume of bone to be removed, i.e. they represent two sections in two distinct planes of the same ruled surface a portion of which is the mantle of the bone surface to be removed.

The guide also includes a guide surface, including the work area, which is the surface of the guide that faces the outer bone surface when the guide is positioned on the bone of the patient to carry out the osteotomy, for example it can be rested on the surface of the bone.

The mantle of the bone volume as defined inside the three-dimensional image is made so that all of the sensitive anatomic structures are avoided and so that an optimal bone volume is obtained in terms of shape, size and thickness. Therefore, the object of the invention is to give the surgeon, who during the operation cannot see the inner structures of the bone, the ability to exactly follow the mantle defined in the three-dimensional image during bone cutting.

For this purpose the guide is designed including a plurality of walls that delimit the work area and such walls are angled very precisely. In other words, at least one of the walls has a face angled so as to be a geometrical extension of a portion of the mantle, i.e. it is also a portion of a second mantle whose segments that generate it are the geometrical extension, forming the same angle, of the segment of the mantle of the bone volume.

In some embodiments, the meaning of "angling at least one of said walls with respect to said guide surface" means that, by carrying out a section of the guide in a plane substantially perpendicular to the guide surface, the segment that is visible and that represents the mantle of the volume of bone to be removed (i.e. the outline of the volume of bone to be removed) and the segment defined by the face of the suitably angled guide wall are the geometric continuation of each other, i.e. they are arranged on the same straight line. The two segments, of mantle and of guide wall, can be contiguous, in the case in which the guide rests on the outer surface of the bone, or a gap can be present between the two, in the case in which a gap is present between guide and outer bone surface. The angle formed between guide surface and the segment belonging to the face of the guide wall defines the cutting angle, i.e. the angle at which a suitable tool will be introduced into the volume of bone so as to detach it along the mantle delimited in the three-dimensional image provided.

Therefore, the fact that a face constitutes a geometric extension of a portion of said mantle includes both the case in which the face is continuous and attached to the mantle when the guide is in operative position for the extraction of the volume of bone, i.e. when the guide rests on the bone surface, and the case in which there is a spacing or gap between guide and bone surface. In this last case the face is a geometric extension after a certain gap.

In this way, for example through a suitable surgical instrument, the cutting direction inside the bone is "set" by the walls of the guide: if the cutting tool rests on the angled walls, i.e. it abuts against the angled face at a predetermined angle, the cutting direction can only be that around the mantle of the bone volume to be harvested by simple geometric construction.

Preferably, the designing of the guide for osteotomy takes place through software installed on a computer. The three-dimensional image relating to the patient's anatomy is processed by the software and consequently the parameters of the guide are determined. The three-dimensional image can be obtained in any way, for example through radiography technology, TAC, PET, etc. The guide can then be made through any known technique, for example 3D printing, based on the parameters determined by the software and for example saved on file.

The software of the invention therefore processes the three-dimensional image of the patient's anatomy, in which the sensitive anatomic elements are identified, i.e. the sensitive anatomic structures, with known recognition algorithms and/or preferably through supervision of the medical or dental personnel. The software therefore determines the possible location, or the possible locations in the case in which more than one is possible in the bone investigated, of the bone volume to be removed having certain dimensions. The dimensions are for example inserted by the operator. In other words, the software of the invention determines the best location where to remove a bone volume based on the value (magnitude) of the bone volume to be removed and where such a volume is available without getting excessively close to the sensitive anatomical structures. In the case in which more than one volume for bone harvesting is available, the operator preferably selects the most appropriate area, taking into account other facts such as the specific anatomy of the patient, the painfulness of the intervention, etc.

Therefore, the guide is made so that a work area is defined surrounded by faces, which constitute a geometric extension of a portion of said mantle of said bone volume.

In other words, the parameters defining the guide are such that it includes a work area that represents with its walls a geometric continuation of the mantle defined by the bone volume selected, i.e. when the guide is used in the operative position to remove the bone volume, facing the outer bone surface portion forming part of the bone volume to be removed, the mantle of the bone volume and walls of the guide surrounding the work area represent a geometric continuation of each other and they are both generated by the same generatrix lines, i.e. they belong to the same ruled surface.

According to a second aspect, the invention relates to a computer-readable medium, including a program for a processor comprising lines of code that, when executed by one or more computers ensure that the one or more computers carry out the method according to the first aspect of the invention.

According to a third aspect, the invention relates to a system including

A computer;

A computer-readable medium containing instructions that, when executed by the computer, ensure that the computer carries out the method of the first aspect of the invention.

In any one of the aspects listed above, the invention preferably includes, in combination or as alternatives, one or more of the following characteristics.

Advantageously, the method for designing the surgical guide, includes:

Generating a computer-readable file including said design parameters of said guide.

In this way, the result of the method of the invention includes a file in which the details for making the guide are contained, details obtained according to the steps of the method outlined above. This file can be written in any format, open or proprietary.

Advantageously, said work area has a perimeter corresponding to the perimeter of said surface portion of said bone identified in said three-dimensional image.

In the case in which the surgical guide rests directly on the outer surface of said bone, the perimeter of the work area coincides with that of the surface portion of the bone identified for the osteotomy.

In the case in which, alternatively, the guide were not to be rested on the bone in the part corresponding to the work area, the latter can have a perimeter that is larger or smaller than the portion of outer surface of bone according to the angling of the walls of the guide.

More preferably, said guide is suitable for being rested on said outer bone surface.

Alternatively, in the method for designing a surgical guide, the step of establishing the parameters of said guide includes:

designing a support for said guide so as to mount a guide made a predetermined distance from said bone surface.

In this case, the guide is raised from the dental surface. Whether a distance or gap is foreseen between the dental surface and the guide depends on the operating conditions and on the anatomy of the patient.

According to a preferred example, in the method of the invention, the step of establishing the parameters of said guide includes:

Defining an upper guide wall, upperly delimiting said portion of surface of said volume of bone to be harvested;

Defining a lower guide wall, lowerly delimiting said portion of surface of said volume of bone to be harvested;

Defining a right side guide wall, delimiting the right hand side of said portion of surface of volume of bone to be harvested;

Defining a left side guide wall, delimiting the left hand side of said portion of surface of said volume of bone to be harvested;

Connecting said guide walls defining said work area;

Angling a face of said upper guide wall, and/or of said lower guide wall, and/or of said right side guide wall, and/or of said left side guide wall with respect to said guide surface as an extension of said mantle.

By connecting the walls of the guide together it is possible to obtain a work area having an oval, circular, elliptical perimeter, etc., or it is possible to form a polygon with two or more sides. The sides can also be curved. The connected walls and the faces made on them can form a single surface without any discontinuity, which preferably thus forms a second mantle, a geometric continuation of the mantle of the volume of bone to be harvested.

The guide therefore includes walls delimiting the surface of the mandible to be cut in the three-dimensional image formed. Given the outline, or perimeter, of the portion of outer surface to be cut, delimited by the work area, each wall of the guide delimits such a perimeter on one side. The two perimeters, of the outer surface to be cut and of the work area, can coincide or be different according to whether the guide is positioned in contact with the outer bone surface. One or more of said walls includes a face angled at said predetermined angle so as to set a work direction, in other words the cutting direction inside the bone. A face can set a plurality of different predetermined angles, and thus work directions: in fact, for each point of the perimeter of the work area a different segment extends and the angle formed by said segment with the guide surface can be equal to or different from the angle formed by the segments adjacent to it. Such a cutting direction is defined by the shape of the volume of bone identified in the three-dimensional image: the volume is set avoiding the sensitive areas and therefore the mantle can have a plurality of different angles with respect to the surface of the bone. The angle is used both to delimit sensitive structures and to define a maximum cutting depth.

Preferably, the method includes the step of

Determining in said three-dimensional image a minimum safety distance between said sensitive anatomic structures and the volume of bone to be harvested identified in said three-dimensional image;

Determining the dimensions of said portion of surface and of said mantle and the position of said volume of bone so as to maintain a distance between said sensitive anatomic structures and said volume of bone to be harvested identified in said three-dimensional image at a value greater than or equal to said minimum distance.

The safety distance thus defined minimises the risks of the sensitive anatomic structures being harmed. The safety distance between anatomical structure and volume can vary according to the anatomical structure itself and according to the patient.

Advantageously, the step of providing a three-dimensional image includes:

Obtaining a copy of a radiograph and/or nuclear magnetic resonance and/or computed axial tomography and/or an echograph of said portion of bone of the patient.

The three-dimensional image can be made through standard volumetric medical investigations that allow all the data to be obtained to make three-dimensional images, through suitable software. Many different investigations can be used together to make a single three-dimensional image.

In an example embodiment, the method of the invention includes:

Angling all of said guide walls by one or more predetermined angles with respect to said guide surface, so as to form a second mantle, a geometrical extension of the mantle of said bone volume, extending from said perimeter of said work area, so as to determine, for each wall, one or more work directions corresponding to one or more cutting directions inside said bone volume to be removed identified in said three-dimensional image.

Having "reproduced" in the guide the mantle of the volume of bone to be removed, i.e. having designed the guide so that it includes a second mantle, a geometrical continuation of the first, so that each segment of the second mantle has the same predetermined angle existing between the corresponding segment belonging to the mantle delimiting the bone volume to be removed and the portion of bone surface, the three-dimensional structure of the volume of bone identified on the three-dimensional image is also reproduced through the guide: the starting surface on which to cut is delimited through the work area and thus a direction in which to penetrate in depth inside the bone is determined, through the second mantle for each point of the perimeter of the work area. In this way, the development in depth of the volume of bone to be removed in the three-dimensional image is established.

The geometric continuation can be without interruptions, i.e. the second mantle can be continuous with the first in the case in which the guide with its walls rests on the outer bone surface, or it can have a gap, in the case in which the guide with its walls is distanced from the outer surface of the bone. In this last case, the second mantle is distanced with respect to the first, but both belong to the same ruled surface formed by the generatrix lines of the first mantle.

Preferably, the method includes the step of angling said face at an angle comprised between 30° and 160° with respect to the guide surface.

The angling of a face as stated above is not constant, and the face can have different angles, since it follows the extension of the mantle of the volume of bone to be removed. Therefore, the angling between the face and the guide surface can be variable within the same face, just as it can also be constant.

More preferably, when a plurality of angles are defined, the method includes the step of defining a first working depth, given by a point or line, the intersection of the segments belonging to said mantle, defining a plurality of cutting directions. In other words, the mantle can close on itself due to the angling of the segments of which it is formed so as to define a maximum depth of the volume of bone to be removed.

The intersection between the various cutting directions defines the point or the segment with maximum depth inside the bone. Therefore, by angling all the faces, one or more per wall, an automatic maximum cutting depth is obtained, called first working depth.

Preferably, the method includes the step of making one or more walls of said guide with a predetermined thickness, i.e. in which the distance between the guide surface and a point along the perpendicular to the latter farthest from it still belonging to a wall of the guide is equal to a certain pre-set value, so as to define a second working depth.

The thickness of the walls can operate as "abutment element" for a cutting tool that works by resting on the inner faces of the walls. The cutting tool acts on the guide resting at the walls and if there is a stop element on the cutting tool that abuts against the end part of the wall of the guide, in other words if a certain distance from a tip of the cutting tool there is an abutment element, when a certain cutting depth is reached, the stop element abuts against one or more of the walls of the guide blocking a further deeper introduction of the cutting tool into the bone. In this way, the cutting tool cannot penetrate inside the bone beyond a certain point, i.e. when the stop element abuts against the top of the wall itself.

According to a preferred example, the step of designing said guide includes the step of providing a guide body in which a window is made, said body comprising a bottom surface that includes said guide surface and said window including said work area.

Therefore, in an embodiment, the guide comprises a body, said body includes a bottom surface with which the guide faces the bone, i.e. it comprises the guide surface, and inside the body a window is made, in other words an opening in the body inside which the portion of bone surface that must be cut is visible.

According to a distinct preferred example, the step of designing said guide includes the step of providing a guide body comprising a bottom surface and one or more side walls, said bottom surface including said work area and said side walls including said guide walls.

In this example embodiment, the portion of outer surface of bone to be removed is covered by a body of the guide, and the perimeter of the surface is cut following the perimeter defined by the guide walls around the body.

According to a further preferred example, the step of designing said guide includes the step of providing a guide body comprising a bottom surface and including a channel closed on itself that divides said body into an outer body and an inner body, said bottom surface including said work area and said channel including opposite inner and outer walls, respectively belonging to said inner and outer body, said outer walls including said guide walls.

In this further example, the body has a channel that delimits the work area. The channel is also used to guide a cutting tool that is inserted inside it to cut the bone along the perimeter delimited by the channel itself. In this example embodiment, the cutting tool is substantially blocked in any further movement other than sliding along the perimeter of the work area by the opposite walls of the channel.

According to a further aspect, the invention relates to a surgical guide made according to the method described in relation to the previous aspect.

Preferably, the guide is such that the thickness of said walls is comprised between 1 mm and 20 mm.

With this range of thicknesses, it is possible to work in most cases, reaching all the depths normally used in bone harvesting.

Preferably, said perimeter of said work area includes a quadrilateral.

The perimeter of the work area can vary greatly, however a quadrilateral, even with curved sides, is preferred.

According to a further aspect, the invention relates to a surgical kit including:

A surgical guide according to the second aspect;

A cutting tool for cutting a portion of bone in cooperation with said guide.

Preferably, said guide of the kit includes a stepped element and said cutting tool includes a stop element suitable for abutting against said step.

Guide and cutting tool form a kit so that each guide can be associated with a personalised cutting tool for that type of guide, for example in which the stepped element is positioned so that the maximum depth reached by the cutting tool having a respective stop element is the desired one for the harvesting.

Alternatively, the same guide can have many cutting tools associated with it having stop elements positioned in different points, so that different depths can be reached according to the design of the osteotomy, or according to the point in the perimeter in which the cut is made.

BRIEF DESCRIPTION OF THE DRAWINGS

The advantages of the invention will become clearer from a detailed description thereof with reference, not for limiting purposes, to the attached drawings, in which:

FIGS. 1a to 1c represent three perspective views from different angles of a three-dimensional image of a portion of mandible relating to a first step of the method according to the invention;

FIGS. 2a to 2c represent three perspective views from different angles of a three-dimensional image of a portion of mandible relating to a second step of the method according to the invention;

FIGS. 3a to 3c represent three perspective views from different angles of a three-dimensional image of a portion of mandible relating to a third step of the method according to the invention;

FIG. 4 represents a schematic drawing in lateral section of a surgical guide made in accordance with the method of the present invention;

FIG. 5 represents a further schematic drawing in lateral section of a surgical guide made in accordance with the method of the present invention;

FIG. 6 represents a schematic drawing of an apparatus for carrying out a part of the method according to the invention;

FIG. 7 represents a schematic drawing in lateral section of a surgical guide according to a further preferred example made in accordance with the method of the invention;

FIG. 8 represents a schematic drawing in lateral section of a surgical guide according to a further preferred example made in accordance with the method of the invention;

FIGS. 9a and 9b represent schematic drawings in lateral section of a step of the method according to the invention;

FIGS. 10a and 10b represent schematic drawings in lateral section of a surgical guide according to a further preferred example made in accordance with the method of the invention;

FIGS. 11*a* and 11*b* represent schematic drawings in lateral section of a surgical guide according to a further preferred example made in accordance with the method of the invention;

FIGS. 12*a* and 12*b* represent schematic drawings in lateral section of a step of the method according to the invention;

FIGS. 13*a* and 13*b* represent two perspective figures of the surgical guide made according to the method of the invention;

FIG. 16 represents a schematic drawing of a step of the method of the invention;

FIG. 17 represents a schematic drawing of a further step of the method of the invention;

FIGS. 21*a*-21*c* represent a further application of the method of the invention.

DETAILED DESCRIPTION OF THE PREFERRED EMBODIMENTS

Figure 14:
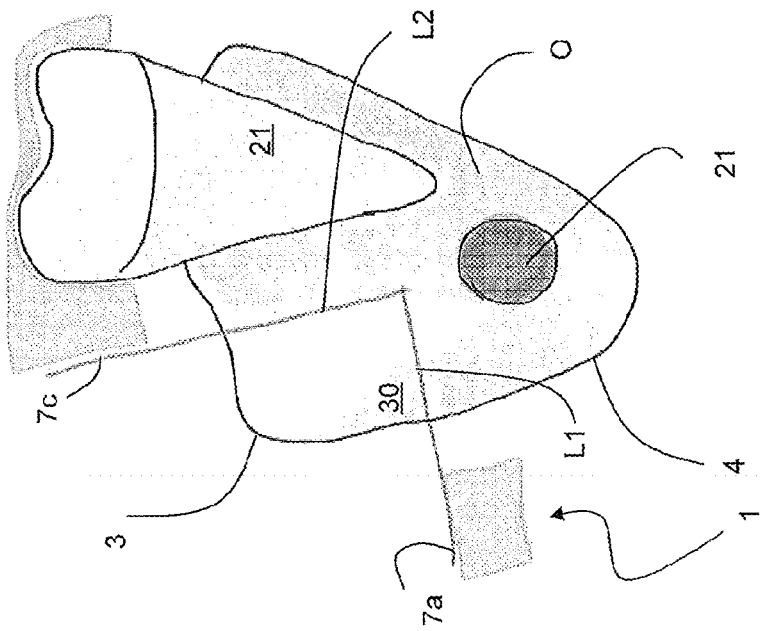
FIG. 14 represents a schematic drawing in lateral section of a surgical guide according to a further preferred example made in accordance with the method of the invention.

Initially with reference to FIGS. 4, 5, 7 to 11*b*, 14 and 15 a surgical guide for performing mandibular bone harvesting is globally indicated with 1.

The guide 1 is depicted resting on a bone O, in particular on a portion of mandible, in which the osteotomy is carried out. The surface 4 of bone O in which the guide is rested is an outer surface of a bone. The figures represent the mandible as the bone, however the teaching of the invention can be applied to any other bone.

In some embodiments, the outer surface 4 is the accessible surface of the bone.

The surgical guide 1 has a configuration that depends on the anatomy of a patient and on the dimensions of the mandibular bone harvesting that are to be carried out in this specific patient based on the bone deficit. Making the guide "dependent on the patient" according to the method of the invention is specified hereafter following a description of its structure.

The guide 1 comprises a body 80 comprising a bottom surface that includes a work area 2, delimited by an outer perimeter 3. The configuration in plan of the outer perimeter 3 of the work area 2 can vary greatly—circular, elliptical, oval, etc. and preferably it includes a polygon with N sides, however the sides of the polygon are not necessarily rectilinear, but there can even be curvilinear portions.

The dimensions of the work area 2 depend on the dimensions of the bone harvesting to be carried out in the patient. In fact, the work area 2 delimits a portion 6 of outer surface 4 in the bone O onto which the guide 1 faces when in use. The work area 2 can be larger, smaller or the same as the portion 6.

Moreover, the bottom surface comprises a surface facing, in a preferred example in contact with, the bone O when the guide is positioned in the patient's mouth, hereafter called guide surface 8. The guide surface 8 includes the work area 2. Preferably, in the case in which the guide 1 is in contact with the surface 4 of bone O, such a guide surface 8 is made so that the resting of the guide 1 on the surface 4 of the mandible is as stable as possible, i.e. preferably the guide surface 8 substantially matches the shape of the outer surface 4 of the bone O where it is rested. In a different preferred example, for example if resting were not possible or difficult in practice, the guide 1 is raised with respect to the bone surface 4, so that a gap is present between the guide surface 8 and the outer bone surface 4, and the guide 1 can for example be anchored to one or more teeth, as exemplified hereafter.

The guide surface 8 is not necessarily flat (even if in FIGS. 4 and 5 it is approximated with a plane for the sake of simplicity of illustration), it can be curved and irregular since it depends on the anatomy of the surface of the bone 4 that does not correspond to a geometrically perfect plane. In FIGS. 7, 8, from 9*a* to 11*b*, 14 and 15 a more realistic representation of the guide surface 8 and of the surface 4 of the bone O is provided.

The guide 1 also comprises in the body 80 one or more walls 5*a*,5*b*,5*c*,5*d* that delimit the work area 2 and that rise up from the guide surface 8. The number of walls depends on the configuration of the perimeter 3, for example in the case of a quadrilateral there are four walls. The walls can also geometrically form a single wall with solution of continuity. In FIGS. 4, 5, from 7 to 11*b*, 14 and 15 just the opposite walls 5*a* and 5*c* are visible.

At least one wall 5*a*,5*b*,5*c*,5*d* of the guide 1, preferably each guide wall, for example as can be seen in FIGS. 4, 5, from 7 to 11*b*, 14 and 15 the walls 5*a* and 5*c*, more preferably also the remaining walls 5*b* and 5*d* (and for whatever number of walls included in the guide 1), includes an inner face 7*a*, 7*b*,7*c*,7*d* facing towards the work area 2 forming a predetermined angle with the guide surface 8. In the case of a guide including an arbitrary number of walls N, at least one of them, preferably more than one and more preferably all, includes a substantially flat inner face forming a predetermined angle. A wall 5*a*, 5*b*, 5*c*, 5*d* can also include more than one face. The angles formed between an inner face belonging to a wall and the guide surface, and the angle formed between another face of another or of the same wall and the guide surface can coincide or be different. However, it is not necessary for all of the walls to include such a face.

It should be understood that the faces 7*a*-7*d* do not have to extend from the perimeter 3 for the entire extension of the wall itself, but just for a portion thereof. There can be other joining surfaces.

Each face 7*a*, 7*b*, 7*c*, 7*d* includes a ruled surface, in other words a surface formed from a plurality of segments, each of which extends from the perimeter 3 of the work area 2. Therefore, for each point of the perimeter 3, a segment extends from it that forms a predetermined angle with the surface of the work area or guide surface. From this it is clear that each face can form a plurality of angles with the guide surface 8, one for each different segment from which it is formed.

In a preferred example, all of the walls 5*a*, 5*b*, 5*c*, 5*d* of the guide include respective inner faces 7*a*, 7*b*, 7*c*, 7*d* and the work area 2 is delimited all around the perimeter 3 by such faces. In this case the faces form a continuous mantle, a mantle that includes a continuous surface around the work area 2. The mantle itself is a ruled surface formed from a plurality of segments each of which forms a defined angle with the guide surface.

Hereafter we will refer just to the structure of the walls 5a, 5c visible in the drawings, however such a description also applies to other N walls included in the guide of the invention 1.

The predetermined angle between the guide surface 8 and the segments forming the inner face 7a,7c is preferably comprised between 30° and 160°. Each face can be angled by a different angle with respect to the angle present between the other faces and the guide surface 8, as represented for example in FIGS. 4 and 5, in which the angle a between the face 7a of the wall 5a and the guide surface 8 is smaller than the angle b between the face 7c of the wall 5c and the guide surface 8.

The value of the angle(s) formed by the segments belonging to the inner faces of the walls 5a-5d depends on the anatomy of the bone from which a volume must be harvested. In FIGS. 7 and 8, various angles are shown: in FIG. 7 a segment of the wall 5a forms an angle of less than 90° with the guide surface, whereas a segment of the opposite wall 5c forms an angle with the guide surface 8 that is greater than 90°. In another example of FIG. 8, both the angles displayed are over 90°.

For each point of the perimeter 3 at each face 7a, 7c it is possible to define an extension of each segment belonging to the face, an extension that extends inside the bone O. In particular, this extension of segment remains angled with respect to the guide surface 8 by an analogous angle to that defined between the face 7a, 7c and the guide surface 8. The extension of this segment inside the bone O along a direction defined by such a predetermined angle a,b defines a work direction inside the bone, as described more clearly hereafter.

In the case of the presence of a plurality of inner faces 7a, 7c, at least one per wall 5a, 5b, each including segments and their extensions angled at a predetermined angle with the guide surface 8, in the same way a plurality of work directions are defined, which can intersect inside the mandible. In FIGS. 4 and 5 such work directions formed by two segments that extend from the inner faces 7a and 7c, are indicated with L1 and L2 respectively, the first being the work direction defined by a segment of the inner face 7a and forming angle a, and the second that defined by a segment of the inner face 7c and forming angle b. As can be seen in FIGS. 4 and 5, the two work directions L1 and L2 meet at a point inside the mandible O.

In the case in which the faces 7a-7d form a continuous wall, i.e. a mantle including a ruled surface, it surrounds the work area 2.

In addition to the guide surface 3, to the work area 2 and to the walls 5a-5d, the guide can include further elements, like for example, in the case of a guide for mandible osteotomy, a dental fixing element 70, for example visible in FIGS. 8 and 10a.

Furthermore, the guide walls 5a,5c in a direction substantially perpendicular to the guide surface 8 have a thickness S (visible in FIG. 5), which may be defined as the maximum distance from the surface of the guide 8 with reference to a direction substantially perpendicular to the latter, which is preferably comprised between 1 mm and 20 mm. Each wall can have a different thickness with respect to that of the other walls, like in the example of FIG. 5 in which the wall 5a is thicker than the wall 5c.

In an example embodiment, the end part of each wall opposite the guide surface 8 defines a stop point for a device (detailed hereafter) suitable for performing the mandible cutting and removal operation, as is detailed hereafter. In particular, preferably one or more walls 5a, 5c include a stepped element or formation 23, substantially on top of the wall itself, for the cutting device to rest on and to block its sliding.

In FIGS. 4 and 5, a first preferred example embodiment of the guide is represented. The body 80 of the guide 1 includes a window corresponding to the work area 2. Substantially, the body 80 is "perforated" and the surface of the hole in plan constitutes the work area 2. The window 2 made in the guide surface 8 is surrounded by walls 5a-5d. The walls therefore surround the window and the inner faces 7a-7d face towards it. The window matches with the portion of surface of bone 6 to be removed. The perimeter of the work area 3 is the perimeter of the window 2. The work directions L1 and L2 indicated therefore correspond to the extension of segments of the face 7a and 7c that, through the window, extend in the bone O.

In the preferred example represented in FIG. 14, the work area 2 and its perimeter 3 are not rested on the outer surface 4 of the bone O, although the guide 1 is. In other words, the guide 1 always comprises a window (work area) 2 delimited by a perimeter 3, but such a perimeter does not coincide with the perimeter 6 of the portion of outer surface 4 of the bone and/or the guide is not rested on it. In fact, between the outer surface 6 and the perimeter 3 of the work area 2 there is a gap. In other words, the guide 1 can include other walls and other faces in addition to the walls and faces delimiting the work area 2 and arranged between the work area and the outer bone surface 4. These further walls, like in the example of FIG. 14, can simplify and help the resting of the guide 1 on the surface of the bone O. The faces 7a, 7b, 7c, 7d of the walls of the guide remain defined as those walls that are a geometric continuation of the mantle of the bone volume to be removed, irrespective of whether there is a gap between the mantle of the bone volume and a further mantle defined by the faces of the walls of the guide. However, in order for this geometric continuity to be present, the two mantles must be generated by the same generatrix lines.

Figure 15:
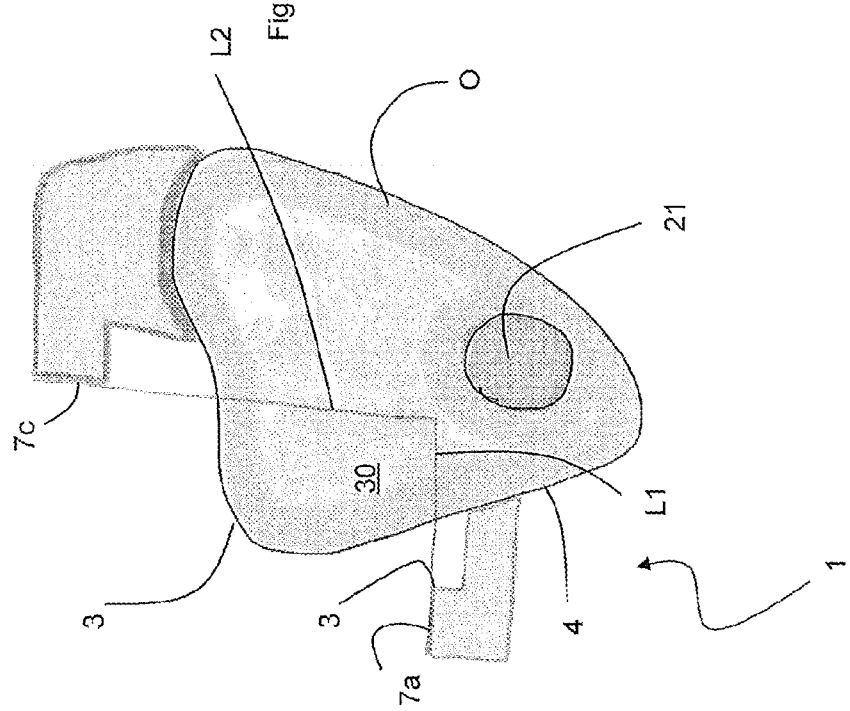
FIG. 15 represents a schematic drawing in lateral section of a surgical guide according to a further preferred example made in accordance with the method of the invention.
Figure 18A:
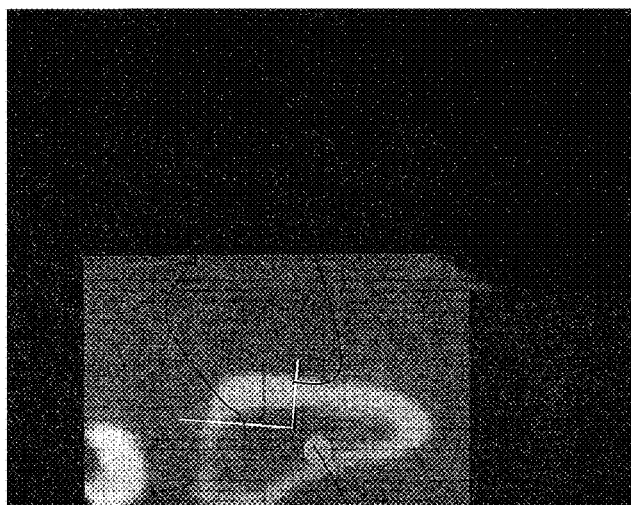
FIGS. 18*a*-18*e* represent a plurality of steps of the method of the invention.
Figure 18B:
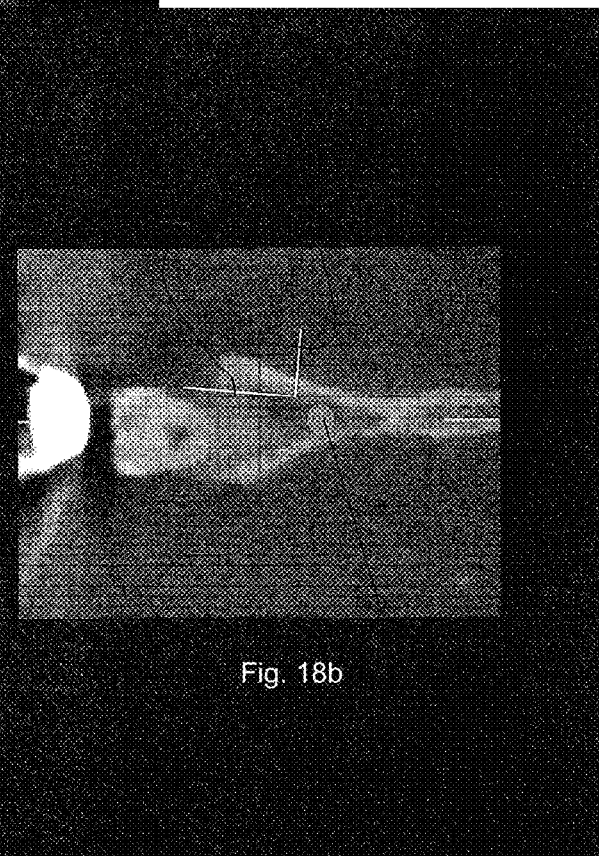
Figure 18C:
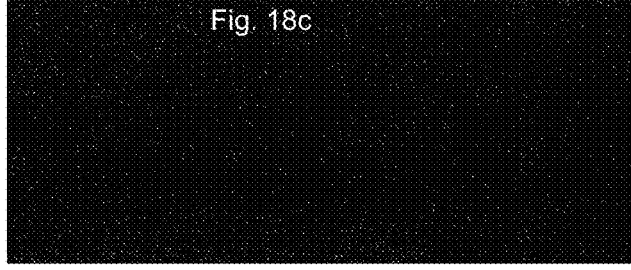
Figure 18D:
Figure 18E:
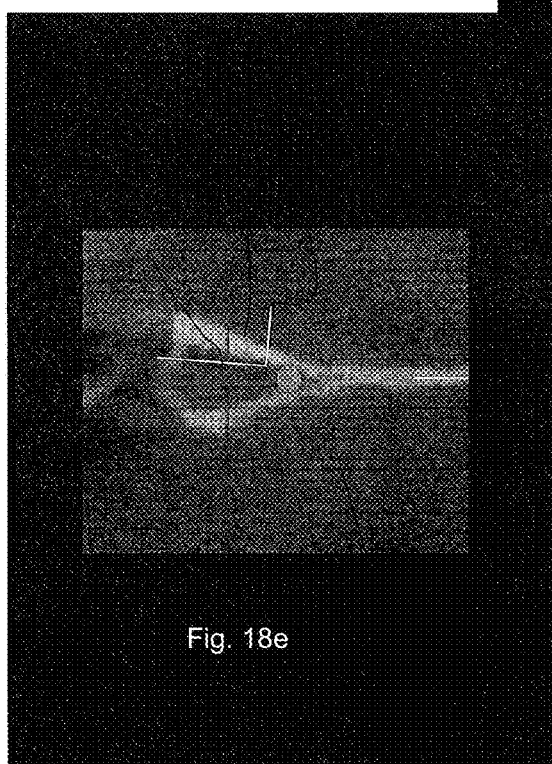

In FIG. 15, the guide 1 is not rested on the bone O in any way, but is raised from it, i.e. there is a certain distance between the bone surface 4 and the work area 2. A type of attachment that allows the guide 1 to still face the outer surface 6 of the bone O, but be raised from it is for example through a dental fixation 70.

In the preferred examples of FIGS. 14 and 15, the perimeter of the work area 2 and the perimeter of the portion 6 of outer surface of the bone O do not coincide. According to the angle of the faces 7a-7d, such a perimeter 3 of the work area 2 can be larger or smaller than the perimeter of the portion of bone surface to be removed. In detail, it is larger when the angle between the work surface and the face is obtuse and it is smaller when it is acute.

In any case, also in the preferred examples of these FIGS. 14 and 15, there is geometric continuity between the generatrices of the mantle 38 of the bone volume 30 and the faces 7a-7d themselves, in other words, the mantle of the volume 30 and the faces 7a, 7b, 7c, 7d are generated by the same generatrix lines, even if there is a gap between the mantle and the faces.

The projection of the perimeter 3 of the work area 2 on the outer surface of the bone O coincides with the perimeter of the portion 6, considering the projection following the generatrices of the mantle. Preferably, considering a three-dimensional surface formed by the generatrices, a surface that defines and contains the mantle of the volume 30 as well as the faces 7a-7d of the guide 1, the perimeter of the portion 6 and the perimeter of the work area are the two perimeters given by the intersection of two distinct planes with the ruled surface formed by the generatrix lines of the mantle of the volume 30 and of the faces 7*a*, 7*b*, 7*c*, 7*d*.

In FIGS. 11*a* and 11*b*, a different preferred example of the guide 1 is represented. The body 80 does not have holes, but in this case the base itself of the body, i.e. the bottom wall, corresponds to the work area 2, a base that is rested on the outer surface of the bone. The perimeter of the bottom wall corresponds to the perimeter of the guide area 3. The body 80 also comprises one or more side walls, which correspond to the guide walls 5*a*, 5*b*, 5*c*, 5*d* that delimit the work area 2. Also in this case the number of walls depends on the configuration of the perimeter 3, as well as on the geometry of the body 80.

At least one of the guide walls includes an inner face 7*a*, 7*c* including a plurality of segments each forming a predetermined angle with the guide surface 8. In this case, the faces face towards the bone surface not to be removed. Unlike the preferred example of FIGS. 4 and 5, in this embodiment, the surface of bone to be removed 6 is "covered" by the work area 2.

Similarly to the previous example, each face includes a ruled surface, in other words it is formed from a plurality of segments, each of which extends from the perimeter 3 of the work area 2. Therefore, for each point of the perimeter, a segment extends from it that forms a specific angle with the guide surface. In the case in which the walls form a mantle, the mantle itself is a ruled surface formed from a plurality of segments each of which forms a defined angle with the guide surface. The mantle is given in this case by the sum of the surfaces of the side walls of the body 80. The work directions L1 and L2 are also displayed in FIGS. 11*a* and 11*b*.

In the example of FIGS. 11*a*,11*b*, the guide surface and the work area substantially overlap, and in the example of the figures they coincide. However, like in the case of FIG. 8, the guide surface can extend further with respect to the work area 2, for example due to the presence of dental fixing elements 70 (in this case not depicted). Alternatively, the guide or just the work area can be positioned a certain distance from the bone surface 4 and the perimeter of the work area therefore depends on this distance or gap and on the angle of the faces since it is such that, when a cutting tool is rested on the faces of the guide, it cuts the bone at the perimeter 31.

In FIGS. 10*a* and 10*b*, a third preferred example of guide 1 is represented. In this example, the body 80 includes a channel 91 forming a closed path that passes through the body 80 for its entire thickness. The channel 91 shaped like a ring therefore divides the body 80 into an inner body 92 and an outer body 93. The channel 91 also includes one or more outer walls 5*a*,5*b*,5*c*,5*d* belonging to the outer body 93 and one or more inner walls 95 belonging to the inner body 92, opposite one another. The outer walls correspond to the guide walls and the portion of guide surface delimited through the outer wall of the channel 91 corresponds to the work area 2. In other words, the work area is formed from a bottom wall of the inner body 91 that rests on the bone plus the area delimited by the thickness of the channel 91. The perimeter 3 is given by the perimeter of the outer walls 5*a*-5*d*.

On the outer walls one or more faces 7*a*-7*d* are thus formed including ruled surfaces in which the segments that form them are angled at a predetermined angle with the guide surface. In the case in which the outer walls of the channel form a single surface with solution of continuity, the channel 91 comprises an outer mantle and an inner mantle facing one another.

Also in this case, alternatively, the guide or just the work area can be positioned a certain distance from the bone surface 4 and the perimeter of the work area, i.e. the position of the channel 91, therefore depends on this distance or gap and on the angle of the faces since it is such that, when a cutting tool is rested on the faces of the guide, it cuts the bone at the perimeter 31.

In FIGS. 13*a* and 13*b*, two overall perspective views of the guide 1 are represented. The guide 1 includes a body 80 that in this case comprises the window 2. The angled faces 7*a*, 7*b*, 7*c*, 7*d* are visible and form a single mantle.

The guide 1 described is made in accordance with the method of the invention.

A volumetric survey is carried out on a patient Pa that needs reconstructive surgery. Such a volumetric survey includes for example a plurality of radiographs, TACs, NMRs, echographs, etc. Any of these techniques can be combined so as to obtain an amount of data that is as complete as possible, also according to the patient and the type of intervention.

According to the type of surgery, it is possible to carry out such surveys with reference to the entire bone involved or just a portion thereof. Hereafter, merely as an example, the bone involved is the patient's mandible.

The result of such a survey or surveys is saved in a memory or memory support (not shown) of an electronic processor 100 schematically illustrated in FIG. 6.

As an example, the results of such surveys can be saved as a volumetric image in DICOM format (.dcm) either as multiple files Dicom dataset or as single file Dicom dataset.

Using suitable software, for example software available on the market like Free for Modelling®, Simplant®, etc., the data of the images saved is processed and a three-dimensional image 20 of the portion (or of all) the mandible of interest is created. The three-dimensional images depict the mandible (or as stated above a portion thereof) and the other anatomical structures such as blood vessels, nerves, dental roots as well as preferably also muscle tissues. Preferably, at least the dental roots and the bone contours of the cavities inside the bone, in which vessels and nerves extend, are depicted in the image.

The 3D image, i.e. along the axes (X, Y, Z), allows the operator to correctly identify the portion of bone on which to carry out the osteotomy, since it is possible to identify both a bone surface and the required bone depth.

According to a preferred initial step, the size of the volume of autologous bone to be harvested to carry out the autologous bone implant is firstly identified in the three-dimensional image. In fact, according to the extension of the "missing" area, it is established how much bone needs to be harvested in order to be able to restore the bone into an acceptable configuration to be able to then perform a dental implant. Therefore, the extension, or rather the volume 30 of bone needed to be removed from the patient is established according to the amount of damage.

In a second step, by the operator, an area of the bone, in the case of the mandible in particular preferably either at the outer oblique line or at the mental symphysis, where to perform the harvesting of the volume of bone necessary with the dimensions defined above is identified in the three-dimensional image 20 of the portion of mandible (or in general of the bone) of the patient. Therefore, the operator evaluates, given the dimensions of the harvesting to be performed, which area is most suitable for such harvesting.

In order to carry out such evaluation in the best way, not only the dimensions of the bone volume to be harvested should be considered. As depicted in FIGS. 1*a*-1*c*, given the volume of bone 30 having dimensions established as described above that it is necessary to harvest, the operator identifies, in the three-dimensional image(s) 20 obtained by the computer from the volumetric surveys, the sensitive anatomic structures 21 of the patient Pa, which can include nerve, vascular, muscle, dental structures, etc. In FIGS. 1*a*-1*c*, the sensitive anatomic structure 21 identified and represented as a tubular element comprises a vascular or fibre bundle. The dental roots 21 are also identified in the same image, another sensitive structure. All of the sensitive structures identified preferably must not be removed or damaged during bone harvesting. For this purpose, preferably the operator establishes what are the minimum vicinity limits to the sensitive structures 21, substantially defining a safety area around them. Preferably, the minimum distance D between each sensitive structure 21 and the volume of bone 30 to be harvested is greater than or equal to 0.5 mm. Such a distance can also differ according to the sensitive structure, i.e. according to the type of structure 21, the minimum distance can be greater or smaller. Furthermore, such a distance can vary according to the complete clinical background of the patient. A representation of such a distance D is given for example by FIG. 4 in which the minimum distance between the sensitive structure 21 and the volume of bone 30 to be harvested is shown.

In the three-dimensional image 20, a portion of bone is then sought, where such a volume 30 can be "positioned in the image" (and therefore removed in the patient) without touching any sensitive structure 21, i.e. in which position of the mandible there is a volume of bone 30 that is a minimum safety distance from all the sensitive anatomic structures 21 identified.

The volume of bone 30 to be removed is delimited by the portion 6 of outer mandible surface having perimeter 31 and extends inside the bone O for a certain depth, which may or may not be constant. The volume to be removed is indicated with 30 in FIGS. 1*a*-1*c* and 3*a*-3*c* and is drawn as a grey volume. From the outer perimeter 31 of the portion 6 of mandible surface, a mantle 38 extends that delimits the side of the bone volume 30. Optionally, the volume is finally delimitated by a bottom surface 39, as detailed hereafter.

The mantle 38 is a ruled surface.

First of all an area is highlighted in the three-dimensional image where the surface of the bone 4 can contain the portion 6 of surface to be removed. Such a portion is highlighted in the image.

The portion of surface 6 consequently defines a perimeter of the osteotomy, i.e. the perimeter 31 surrounding the surface 6 of mandible to be removed belonging to the volume 30. Such a perimeter 31 is preferably a geometrical figure including:

a rear or right side limit 32,
a front or left side limit 33,
a lower limit 34,
an upper limit 35.

The perimeter can have any configuration, and in a plan view it can be circular, elliptical, oval or it can include a polygon with N sides, which can even be curvilinear.

As stated above, the perimeter 31 may not be arranged in a single plane.

Moreover, the mantle 38 extends from the perimeter 31: the mantle is defined by the surgeon or by the operator so as to obtain a bone volume of the desired thickness but that at the same time avoids all of the sensitive anatomic structures 21 included in the bone O. The mantle is therefore formed as a ruled surface, i.e. as a union of a plurality of segments. Each segment extends from a point of the perimeter 31 inside the bone O. The angle between the segment and the portion of surface of bone 6 to be removed can be constant for a portion of perimeter, or it can change for each point of the perimeter.

The mantle 38 can be considered divided into many walls, given the described configuration of the perimeter 31. In the case in which for each wall the segments all form the same angle, it is possible to define a work direction for each wall, as identified in FIG. 2 by the planes L1,L2,L3 and L4 that from the portion of perimeter at the rear or right side 32, at the front or left side 33, at the lower side 34, and at the upper side 35 extend inside the bone to delimit the shape of the mantle 38.

According to the angles defined by the various segments forming part of the mantle 38, it can be closed on itself or open. In the case of a closed mantle 38, the various segments can intersect one another at a point or at one or more portions according to the angles and/or the geometry. The point or intersection lines between the various segments determine a depth P of the volume 30 inside the bone. For example, in FIGS. 4 and 5, the volume of bone 30 includes the portion of bone surface 6 and the mantle 38, the segments of which along the directions L1 and L2 are displayed, intersecting with one another at a point. The distance between the point of intersection and the surface 4 determines the depth P of the volume 30.

Alternatively, in the case in which the segments of the mantle do not intersect one another and therefore there is an "open" mantle, or in the case in which there is an intersection, but the depth of the volume obtained with the intersection is excessive, the volume 30 includes an additional bottom wall 39, which closes the mantle 38 on the opposite side to the portion of outer surface 6 of bone. The distance between the portion of outer surface 6 and the bottom wall 39 in this case determines the depth of the volume 30. This case is shown in FIGS. 12*a* and 12*b* and the depth is called P2. The depth can vary inside the volume and what is displayed is the maximum depth.

Preferably, the bottom wall 39 of the volume 30 is made by following the lines or natural contours present in each bone O of least resistance, i.e. "bone planes" in which the bone most easy tends to detach when forced.

Each of these geometric limits defined above of the volume 30, according to a preferred example of the method of the invention, has a corresponding one in the guide 1.

In particular, the method foresees the step of designing the guide 1 and defining its parameters so as to comprise the work area 2 that is coupled with the portion 6 of outer surface of the volume 30 to be removed. In the case in which the guide rests on the outer surface of the bone, the area and perimeter of the work surface matches with the area and perimeter of the surface portion to be removed. Otherwise, such a perimeter and area of the work area 2 are larger or smaller than the area and perimeter of the portion 6 of outer surface 4 of bone to be removed, according to the angle that is given to the faces 7*a*, 7*b*, 7*c*, 7*d* of the walls of the guide. Knowing the distance from the outer surface of the bone 4 at which the guide is arranged and the angle of the faces, the perimeter of the work area can be easily calculated. Moreover, the guide 1 includes one or more walls 5*a*,5*b*,5*c*,5*d*, which surround the work area 2 and which, when the guide is rested in or facing the surface to be removed, delimit the perimeter 31 of the portion of surface 6 of the volume 30 to be removed. Substantially, the walls surround the work area 2 having an inner perimeter 3 matching with or corresponding to the perimeter 31 of the volume 30 when the guide thus designed is placed over the portion 6 of mandible surface to be removed. As depicted in FIGS. 2a-2c, in a preferred example embodiment, four distinct walls 5a-5d are made at the right side limit 32, at the left side limit 33, at the lower limit 34, and at the upper limit 35, respectively, of the surface 6 belonging to the volume 30.

Furthermore, as stated above, the volume 30 of bone to be removed and identified in the three-dimensional image 20 has a depth, which can be variable, along the plane substantially perpendicular to the portion 6 of mandible surface. In order to obtain such a depth, the guide 1 must be designed so that at least one wall 5a,5b,5c,5d of the guide includes a face 7a,7b,7c,7d configured in the described way.

It is also desired not only for the desired depth to be reached, but for this depth to be reached following certain directions inside the bone: for example, for the same depth it is possible to have totally different configurations of bone volume 30 removed.

The configuration of the walls, and therefore of the faces 7a, 7b, 7c, 7d, of the guide 1 is determined by the configuration of the mantle 38 of the bone volume 30.

The volume 30 extends inside the mandible along the directions that are substantially "extended" outside the surface of the bone 6 and such a direction is "set" by the segments belonging to the faces of the guide, so that a cutting tool can actually remove just the volume 30 from the mandible following the directions set by the guide.

Therefore, the guide is made so that the face(s) 7a, 7b, 7c, 7d make a geometrical extension, which can be an extension including a gap in the case in which the guide is distanced from the bone surface 4, of at least one part of the mantle 38. More preferably, the guide 1 includes one or more walls including one or more faces that make a geometrical extension of the entire mantle 38. These faces are represented in FIGS. 2a-2c. The geometrical extension is no other than the continuation, possibly separated by a gap, of each segment of the mantle 38 outside the bone surface 4 for a desired portion to form the thickness S of the walls of the guide. In FIGS. 2a-2c for each limit of the perimeter 32-35 a plane crossing the perimeter and following the border of the mantle 38 is highlighted that is partially outside and partially inside the bone: in this example the part of planes inside the bone of the planes L1-L4 defines the mantle 38 of the volume 30, whereas the part of planes outside the bone O determines the mantle formed by the faces 7a-7d of the guide.

In this preferred example, a second mantle is therefore formed in the guide 1 given by the union of the surfaces of the various faces 7a, 7b, 7c, 7d.

The angle that the face 7a, 7b, 7c, 7d forms with the bone surface 4 when the guide 1 is rested on or faces the bone O corresponds to the angle with which the cutting tool (for example a piezoelectric tool) must engage the portion of bone surface 6 for each limit 32, 33, 34, 35 previously defined. In other words each limit of the volume 30 is taken into consideration in the design of the guide 1 like the presence of a wall that not only delimits a part of the perimeter 31 of the portion of surface 6, but also defines in what way the cutting tool, i.e. in what direction, will penetrate inside the bone in its removal. This allows extremely accurate work on the planes X-Y-Z.

In the design of the guide 1 a depth limit is also optionally defined on the work plane of the cutting tool, i.e. the maximum depth of penetration of the tool from the surface 6 inside the bone. Preferably, the maximum depth is comprised between 0.5 mm and 20 mm, defining the maximum depth as the maximum distance inside the bone in a direction substantially perpendicular to the outer bone surface 4. The maximum depth is preferably determined by the thickness itself S of the walls of the guide 1. The variability in the working depth depends on the specific anatomy of the area, on the point of intersection of the work planes, on the safety limit selected by the surgeon with respect to the sensitive structures and on the needs of the treatment plan (size of the defect/bone block). This maximum depth is determined by making a stepped configuration 23 on one or more walls of the guide 1, in a position substantially opposite the guide surface 8.

The thickness of the walls of the guide 1 can be variable among the various walls and also within the wall itself, i.e. the thickness of a single wall may not be constant. An example of this type of embodiment is given in FIGS. 12a and 12b. As represented in FIG. 12a, different thicknesses can lead to an identical depth inside the bone due to the geometric configuration of the portion of bone surface 6 part of the volume 30. In other words, the bottom wall 39 is substantially flat even if the thickness of the walls of the guide 1 is variable. Alternatively, as can be seen in FIG. 12b, the depths can vary and the bottom wall 39 of the volume 30 can also not be flat.

Moreover, the depth limit can also be less than the depth in which there is intersection of the various work planes. This depth limit is detailed more hereafter.

Through the software resident in the processor or computer 100, a surgical guide 1 is generated virtually, which respects all of the parameters defined up to now. The surgical guide 1 comprises:

one or more walls 5a, 5b, 5c, 5d having variable thickness with respect to the guide surface 8, preferably between 1 mm and 20 mm so as to correspond to the limits 32-35 defining the perimeter 31;

one or more inner faces 7a, 7b, 7c, 7d defined in said walls, delimiting the work area 2 and having variable inclination with respect to the other faces if present (according to the design developed for that specific cutting plan);

each face of the guide preferably having a length from the perimeter 3 of the window 2 from 1 mm to 20 mm (according to the design developed for the working depth on that specific cutting plan). The length of the face is defined as the length between two points on the perimeter 3 that delimit it.

In FIGS. 3a-3c the guide 1 made "virtually" through the software following the steps described above is represented around the volume 30 of bone to be harvested. As can be seen, the perimeter 3 of the work area 2 in the guide coincides with the perimeter 31 of the surface of mandible to be harvested. The guide made through the invention is made virtually and depicted and displayed through, for example, a monitor in the computer 100 or preferably rendering.

According to a preferred embodiment, the step element 23, which includes an outer face 11a, 11c, of the guide 1, having a length preferably comprised between 1 mm and 5 mm, arranged substantially perpendicular to the inner face 7a, 7c is also designed in a wall of the guide. The step element therefore includes a further outer face, opposite that 7a, 7b, 7c, 7d delimiting the work area 2, suitable for acting as abutment element for a stop element made in a cutting tool, as detailed hereafter. The remaining portion of wall not facing the window 2 includes, in addition to the outer face 11a, 11c a joining surface 12a, 12c with the guide surface 8. Such a joining surface, preferably not being a work surface, i.e. not being used to define the characteristics and dimensions of the volume of bone to be removed, has an arbitrary configuration.

Furthermore, the guide 1 preferably includes an opening 66 (or many openings) visible in FIG. 13b in which a suitable fixing means can be inserted to lock the guide to the surface 4 of the mandible. For example, the guide includes a hole/holes for an osteosynthesis screw for stabilizing the guide at the bone plane (to be inserted with a dedicated kit).

As also seen it is possible to make dental fixing elements 70 in the guide 1 for resting on the teeth to improve the fastening of the guide to the patient's mandible.

From the outlined method, it is clear that the guide depends exclusively on the anatomy of the patient and on the dimensions of the bone harvesting to be performed, and therefore the surgical guide is unique and specific to the patient in question (substantially customized). For a new patient Pa, it is necessary to design a new guide.

As stated above, the software designs the guide making it possible to define a bone volume 30 delimited by a portion of surface 6 of mandible and by a mantle 39: what is designed on the three-dimensional image 20 then corresponds to the real volume harvested 30.

An example of such software that processes the 3D image described above is now described with reference to FIGS. 16, 17 and 18.

The 3D image 20, for example a file of a TAC of the mandible of a patient as displayed in FIG. 16, is imported inside the processor 100 from a suitable memory support where it had been saved. Such a memory can for example include a medical CD of the patient Pa. Alternatively, such an image 20 can be downloaded from the internet or intranet.

Optionally, a defect on which it is wished to carry out the autologous bone implant is measured, i.e. its dimensions are determined (for example both the linear and volumetric size). These measurements can alternatively be provided by the doctor or measured directly on the patient and not detected from a measurement of the image 20 by the software of the invention. The measurements of the defect substantially correspond to the measurements of the volume 30 of bone O to be harvested and/or the perimeter 31 of the portion 6 of bone surface 4 to be harvested.

In the image 20, again through the software in the computer 100, the sensitive structures 21 are identified, which are, for example, directly highlighted in the file of the image 20 so as to always be seen by the operator. Such sensitive structures 21 can be the mandibular channel, the mental foramen, the dental roots, etc. Of course, the type of such structures varies according to the area of the skeleton where it is wished to harvest the volume of bone for the transplant. The sensitive structures 21, visible in the previous figures, are not represented in FIGS. 16-18.

The sensitive structures 21 are indicated and highlighted by the software of the invention preferably in cooperation with an operator, for example a surgeon or dentist. For example, the operator indicates within the three-dimensional image what bone density must be considered as "tooth", from which the software highlights all of the "tooth" areas, just as the nerves are identified in a section by the operator and then set for continuity by the software.

In any case, any routine able to identify the sensitive areas 21 from the image 20 with or without the contribution of the operator can be used in this step of the method of the invention, The donor site is then selected, i.e. the site from which to remove the volume 30 of bone necessary to repair the measured defect. The area of the donor site is determined based on an evaluation of where it is possible to harvest a volume of bone having the linear and/or volumetric dimensions necessary to repair the defect at the same time without involving the sensitive structures 21 identified.

The software of the invention can propose one or more positions in the bone O where it is possible to harvest the volume of bone 30 required having the desired dimensions and a desired distance from the sensitive structures. Among the various proposals, the operator determines the most appropriate area, taking into account further parameters, such as the patient's anatomy, the painfulness of the intervention, the difficulty thereof, etc.

Preferably, safety margins, i.e. the minimum distance D that must be present between the sensitive structures 21 (not visible in FIGS. 16 and 17) and the volume 30 to be removed are also set by the operator, or are already set as default. Possibly, it is foreseen by the invention for the software to generate an alarm signal, for example audible, in the case in which the operator and/or the software tries to position the volume 30 to be removed too close to the sensitive structures 21. The distance D is for example equal to 0.5 mm or 1 mm, etc. The distance D is programmable and can also vary according to the type of sensitive structure (i.e. according to the category of sensitive structure, like nerve, tendon, etc.) and it is possible to establish a different minimum safety distance in the software of the invention.

Having identified a suitable site, i.e. an outer surface of bone with a sufficient extension in an area of bone that has a sufficient thickness to be able to extract the desired volume therefrom, the volume 30 must be delimited, not only by the portion 6 of outer surface of bone, but also by the mantle 38 inside the bone.

For this delimitation and definition of the mantle, having determined the position of the portion of bone surface 6, a plurality of two-dimensional images are preferably selected, such images being sections of the three-dimensional image, sections preferably obtained through planes substantially perpendicular to the portion 6 of outer bone surface identified for harvesting. In FIGS. 16 and 17, broken lines are used to indicate a plurality of planes S substantially perpendicular to the bone surface 4 indicating such sections at the portion 6 identified. These planes S may or may not be parallel to each other. FIG. 17 includes a plurality of inserts representing such sections, shown in enlarged scale and detailed hereafter with reference to FIGS. 18a-18e.

A spacing between the various section is thus established, either by the operator or directly set in the software, i.e. the distance between the various planes S of FIGS. 16 and 17. In other words, the mantle 38 of the bone volume 30, once the portion of outer surface 6 of bone has been identified, is delimited by defining its extension in set intervals in plans S substantially perpendicular to the portion 6.

These sections S are in the example depicted perpendicular along the donor surface, and in the image of FIG. 17 they are represented as broken lines substantially perpendicular to the curved line that follows the progression of the outer oblique branch/line of the mandible.

The spacing between one plane and the other of these sections is for example every 0.5 mm-1 mm-1.5 mm etc.

On each section, for example on the sections represented in the inserts of FIG. 17, cutting lines L1 and L2 are selected that represent the outline of the mantle of the volume 30. With reference to FIGS. 2a-2c, the cutting lines L1 and L2 that are selected here are sections of the cutting lines that will thus determine the faces 34 and 35 of the guide 1 represented here. The cutting lines are preferably "double" in other words they are thickened by the thickness of the cutting tool (selected for each line). In the delimiting of the volume 30 the software takes into account that the cutting tool used for removing the bone volume 30 has a non-negligible thickness and therefore an external line $L_{1ext}$ and $L_{2ext}$ (not depicted) defining a face outside of the bone block 30 that represents the osteotomy line, and an inner line $L_{1int}$ and $L_{2int}$ (not depicted) at the volume that defines the real limit of the volume in net of the osteotomy, i.e. the actual mantle 38 of the volume 30, are determined. In the figures, however, a single cutting plane $L_1$ or $L_2$ is indicated for the sake of clarity.

The definition of the cutting lines or planes, and therefore of the mantle 38, is carried out on each section S. Once the most appropriate cutting line L1 and L2 of the mantle 38 has been defined in a section, by the software, preferably on the section after the one where the cutting lines have been defined, the already-existing cutting lines, i.e. coinciding with the cutting lines (with the same angle) that had been selected in the previous section, are automatically proposed. These "automatically proposed" cutting lines L1 and L2 can be confirmed or modified by the operator.

An example is displayed by FIGS. 18a-18e that represent, in enlarged scale, the inserts of FIG. 17. Each FIGS. 18a-18e therefore represents a section of FIG. 17 along the plane S outlined and highlighted.

In FIGS. 18a-18e the mandibular nerve 21 is identified as a sensitive anatomic structure to not involve in the volume of bone 30 to be removed.

For each section in the plane S represented in FIGS. 18a-18e, the cutting lines L1 and L2 are identified. Preferably, just the cutting lines L1 and L2 for the first section (FIG. 18a) are established by the operator, the other cutting lines for the next sections of FIGS. 18b-18e are determined automatically by the software. In every section, however, the operator can modify the cutting lines L1 and L2 by varying their position and/or angle.

The set of cutting lines represents the mantle 38 of the volume 30, which includes one or more cutting planes. In other words, the software according to the invention interpolates, through a plane or a curvilinear surface, all of the lines L1 and all of the lines L2 with each other, so as to form a union surface of lines L1 and a union surface of lines L2. The three-dimensional structure of the mantle 38 of the volume 30 from the single sections S in which "segments" are defined (the cutting lines L1 and L2) is generated automatically by the program that, through a continuous surface, joins the lines L1 together and the lines L2 together. Such surfaces, one for the lines L1 and one for the lines L2, extend substantially locally perpendicular to the lines L1 and L2, and join the line L1 established in a section S with the line L1 of the previous and next section (which are at a distance equal to the distance between the two planes of the two sections), the line L2 with the line L2 of the previous and next section and this for each section, thus generating a surface connecting all of the lines L1 and a surface connecting all of the lines L2 having a length equal to the distance between the first and the last section.

According to the number of sections S, since they are preferably spaced apart as stated with a predetermined pitch, in which the cutting lines L1 and L2 are identified that correspond to the mantle 38 of the volume 30 of bone to be removed, the length—in the case of FIG. 17 front to back—of the volume of bone of the harvesting is determined.

Advantageously, gradually proceeding one section after the other to delimit the mantle of the volume 30 of bone, a window or a pop-up or another display appears in a screen of the computer 100 that shows the envelope of the lines L1, L2 up to that set time, thus it is always possible to keep the total size of the volume 30 of bone, as well as the linear size thereof, under control.

Since in this depicted case it was established to work on sections S obtained through planes that are parallel to each other and substantially perpendicular to the surface of the bone 4, through the cutting lines two surfaces are defined delimiting the volume of bone 30 substantially facing each other. However, there are no closing surfaces of the volume, i.e. the surfaces that delimit the mantle 38 of the volume of bone 30 in a plane substantially parallel to the section planes at the last and first section made S. The software preferably automatically generates two end surfaces to close the surfaces that have been defined by continuously joining the cutting lines L1 and L2 defined in the various sections. For example, these two further surfaces are surfaces that connect together the cutting lines L1 and L2 of the first and last section, respectively, substantially in the section plane S itself. However, a distinct construction can be foreseen, i.e. new sections can be made, perpendicular to those generated up to now, to establish the cutting planes at the two extremities of the mantle 38.

In this way, the mantle 38 is calculated, which is a continuous surface. This continuous surface is formed by a plurality of segments, or generatrix lines, which are virtually extended outside of the bone surface 4. In other words, the segments generating the mantle 38 are "elongated" outside of the bone.

The faces of the guide are given by a section of such an extended mantle. The geometric surface outside of the bone is sectioned at a certain distance or in contact with the surface of the bone, and this surface represents the faces of the guide.

The software generates a guide of constant height and constant thickness from these parameters. Height and thickness can be modified.

The guide is the projection outside the bone surface of the cutting planes, in other words, the parameters of the guide are determined by extending the cutting lines outside the bone, generating a new mantle obtained in an analogous manner to what has been described above. Such cutting lines extended outside are connected together, as described relative to the inside of the bone, so as to form the faces 7a-7d of the guide 1. The cutting lines are connected together to form the mantle either immediately in a position in contact with the bone surface 6 in the case in which the final guide is rested on it, or a set distance from the surface, according to the distance at which the guide is positioned from the outer bone surface 4.

In an optional step of the method of the invention, if the depth control, i.e. the control of the maximum depth at which a tool can be inserted inside the bone by operating on the guide, is associated, the height of the guide (i.e. its distance for each point from the surface of the bone 4 or in other words the length of each face) is determined taking into account the depth of the volume 30 of bone to be removed and thus the maximum depth at which the cutting tool can be introduced into the bone itself.

Having thus determined the second mantle that must be defined by the faces of the walls of the guide 1, the guide surface 8 that must face or rest upon the bone surface 4 is defined. Such a guide surface 8 is configured taking into account the bone structure that delimits the portion of bone surface to be harvested.

Alternatively or in addition, it is possible to define the dental support elements or surfaces 70, in the case in which the guide in order to fix stably needs to anchor to the patient's teeth. Also in this case, the anatomy of the patient is evaluated around the portion and volume of bone to be harvested.

Furthermore, the position of the holes for the attachment screws, i.e. for the screws for anchoring the guide to the patient's bone O, is preferably established.

Once guiding is complete, preferably the operator evaluates the guide as a whole by making minor changes for its complete adaptability to the specific anatomy of the patient.

An electronic file is thus generated, in the most appropriate format, containing all the data for correct generation and/or displaying of the guide, i.e. a file containing all the parameters for making the guide 1 as outlined above.

The guide thus designed is thus preferably made through any known process suitable for the purpose. For example, the guide 1 can be made from the three-dimensional design through laser-sintering or through 3D laser printing. The material from which the guide is made can for example be polyamide, titanium, etc.

In use, the gum (or the skin of the patient under which the bone involved is located) of the patient is cut and the bone O is exposed, i.e. the outer surface of mandible where the osteotomy is performed. The guide 1 is then rested through the guide surface 8 on the surface 4 of bone so as to make the part of the bone that must be removed visible to the operator; alternatively, it is suspended and faces opposite the bone surface to be removed. In fact, without the guide 1 it is very difficult for the operator to reconstruct the underlying anatomical structure highlighted by the surveys that led to the three-dimensional reconstruction of the patient's anatomy by viewing the patient's mouth.

The guide 1 is then rested on or faces the surface of the bone O and is preferably screwed onto it, through suitable screws as described above. Alternatively or in addition, the dental fixing element 70 is used to minimise the displacements of the guide with respect to the bone of the patient. A suitable cutting tool 50 (displayed schematically in FIGS. 5, 9b, 12a and 12b), for example piezoelectric, is rested on each face 7a,7b,7c,7d of the guide 1. The tool 50 generally comprises an elongated body 51 and a stop element 52, suitable for abutting on the stepped configuration 23 of one of the walls 5a,5b,5c,5d, or on the end part of the wall itself in the case in which there is no step. In the end part of the elongated body 51, the cutting means 54, such as a milling cutter, a blade or a laser suitable for cutting the bone O is present. Preferably, the distance between the stop element and the end part where the cutting means 54 is present, is comprised between 2 mm and 30 mm.

Preferably, the stop element 52 has an adjustable distance with respect to the end part of the elongated body 51, or a plurality of cutting tools 50, each with a different distance between stop element and cutting means is available.

The tool 50 is positioned with the elongated body 51 abutting laterally against a face of the guide 1 and the end part with the cutting means 54 resting on the bone O. The cutting tool then cuts the bone in the direction given by the position of the face 7a, 7b, 7c, 7d where the elongated body abuts with a pressure given by the opposite end to that at which the cutting means is present. In other words, the cutting means 54 penetrates into the surface 6 along the cutting direction determined by the segment belonging to the face, as a geometrical extension outside the bone of the mantle 38 of the volume 30.

The cutting depth, i.e. the depth at which the tool can be simply abutted with the elongated body against the face of the guide, depends on the stop element 52: it is not possible to penetrate inside the bone for more than a given depth since the stop element abuts in the step 23 formed in the wall of the guide 1 and it is no longer possible for the elongated body 51 to translate along the face 7a, 7b, 7c, 7d.

Alternatively, in the case in which the cutting directions intersect one another, the maximum cutting depth is not reached sine the volume of bone 30 detaches before having been separated from the bone O.

Preferably, the tool 50 is rested on each face of each wall of the guide, until the portion 6 of surface of the bone O is cut along the entire perimeter 31.

As stated above, the maximum depth of the harvesting is given both by the positioning of the stop element 52, and by the mutual angling of the cutting directions L1, L2, L3, L4: in the case in which the cutting directions given by the various faces and by the angling with the guide surface 8 as described above, intersect one another, the maximum depth of the harvesting can be given by the point of intersection of the directions, according to which of the two depths (that given by the intersection of the cutting directions and that given by the interaction of the stop element with one of the walls of the guide) is smaller.

In the case in which the directions L1, L2, L3, L4 do not intersect, or in the case in which the distance given by the stop element is less than the depth determined by the intersection of the planes, the bone volume is detached along the bottom surface 39. The bone in this direction can be easily detached since as stated the bottom wall follows the natural breaking lines of the bone. An example of this situation is given in FIGS. 9a and 9b. In FIGS. 9a and 9b the cutting directions L1 and L2 intersect actually outside the bone O. Therefore it is not possible, without damaging the patient, to harvest a bone of such thickness. The volume 30 is therefore delimited by the bottom wall 39. With the cutting tool 50 the bone is cut until the maximum depth permitted by the mutual cooperation of the thickness of the walls of the guide 1 and by the stop element 52 is reached. The guide 1 and the cutting element 50 are made so that "at end of stroke", i.e. when the stop element is in abutment against the stepped element 23 of one of the walls 5a,5b, 5c,5d of the guide, the bottom wall 39 is reached.

Once the bottom wall 39 has been reached everywhere, i.e. for each point of the perimeter 31 of the portion of surface 6 to be removed, the volume of bone is made to detach, with suitable tools that are not shown, and it is easily separated from the remaining bone 30.

The same process is carried out with reference to FIGS. 12a and 12b in which a guide 1 with channel 91 is used. The cutting tool 50 is inserted in the closed channel 91 and crosses its entire extension, having thus crossed the entire perimeter 31. The bone volume 30 is then detached as described above, according to whether the maximum depth is that given by the intersection point or line of the cutting directions or by the stop element. In this configuration, the presence of the channel 91 limits the possibilities of movement of the cutting tool 50 and therefore minimises possible risks of accidental movement thereof from the desired perimetral path 31.

Similarly, in the case in which the guide has a body 80 that covers the portion 6 of bone surface (see FIGS. 10a and 10b), the cutting tool 50 is also in this case rested on the guide walls 5a,5b,5c,5d which in this case are the side walls of the body 80. The cutting tool 50 crosses the entire perimeter 31 of the portion of surface 6 always remaining rested against the side walls del body 80.

Therefore, all of the sensitive anatomic structures 21 identified in the three-dimensional image of the patient stay protected, since the guide 1 made for that specific patient as a function of their anatomy and the size of the bone volume to be preserved imposes a "guided path" on the operator. In fact, both the extension of the surface to be cut in the bone (that in the area 2) and the depth and the direction inside the bone to be followed are determined by the guide. The depth is given either by the stop element in the tool or by the intersection of the work planes, whereas the direction in depth is given by the predetermined angle or angles between the various faces of the walls of the guide and the guide surface 8.

Figures 19A, 19B, 19C:
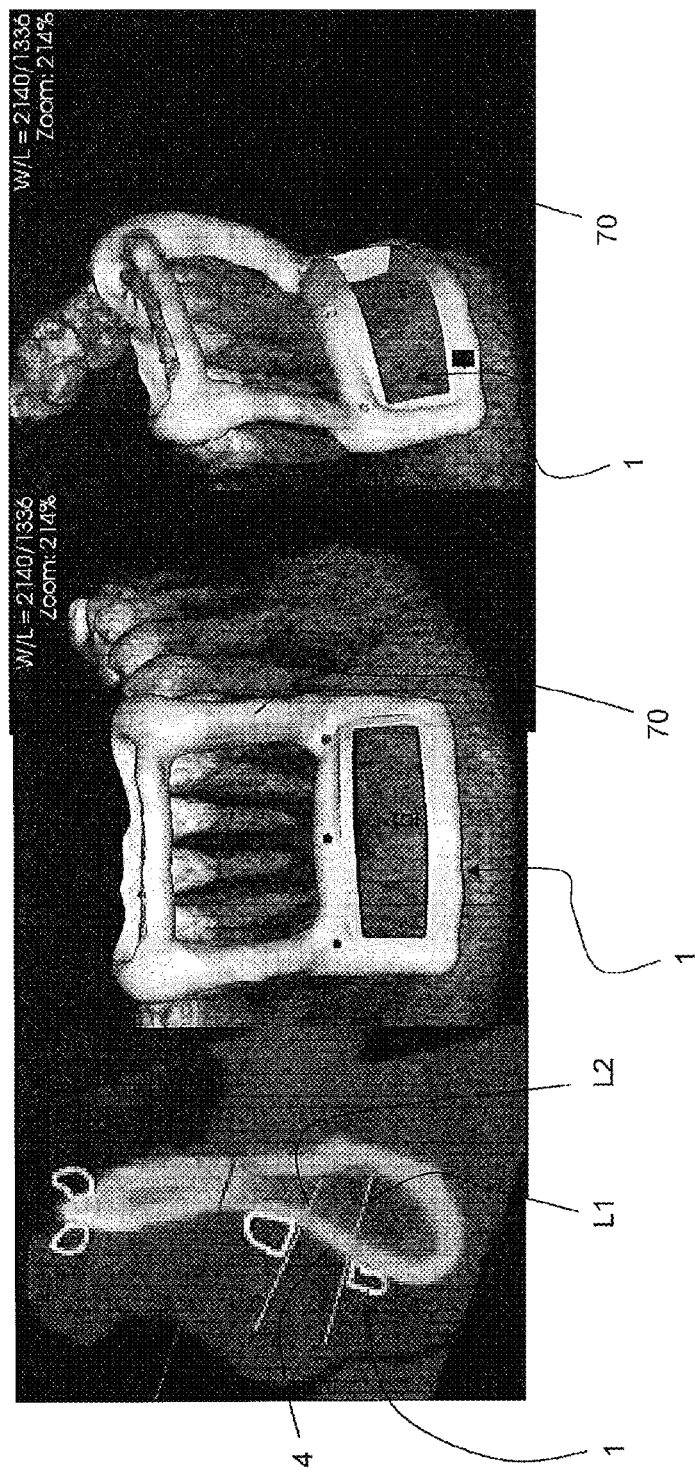
FIGS. 19*a*-19*c* represent a first application of the method of the invention.

In FIGS. 19*a*-19*c* a first use of the guide 1 is represented. In this example, as highlighted in FIG. 19*a*, the guide is made by defining two cutting planes L12 and L2 that are constant for substantially all of the sections S of which FIG. 19*a* represents an example. In other words preferably the surface connecting together all of the lines L1, and additionally more preferably also the surface connecting together all of the lines L2, are planes. The guide 1 in its use is directly rested on the outer bone surface 4, so that the perimeter 3 of the work area substantially coincides with the perimeter 31 of the portion 6 of bone surface to be removed.

The guide includes not only the walls including the surfaces 7*a*, 7*b*, 7*c*, 7*d*, but also a dental fixation element 70 for better anchoring of the guide 1 itself.

In this case the guide 1 is made to remove a volume 30 of bone in the chin.

Figure 20A:
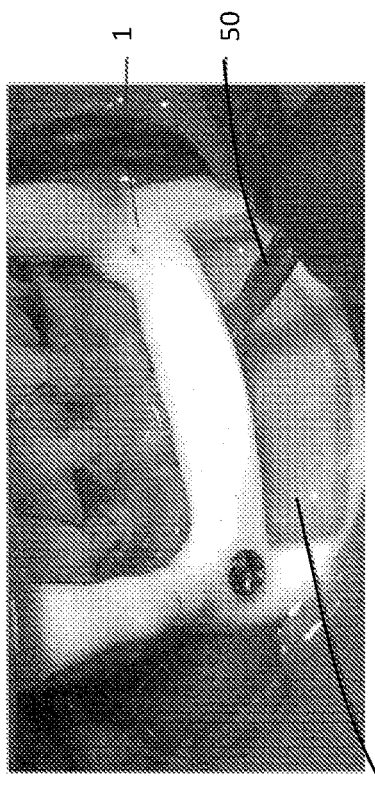
FIGS. 20*a*-20*c* represent a further application of the method of the invention.
Figure 20C:
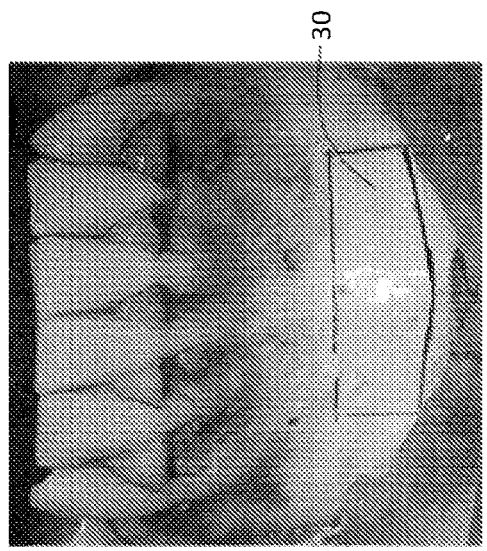
Figure 20B:
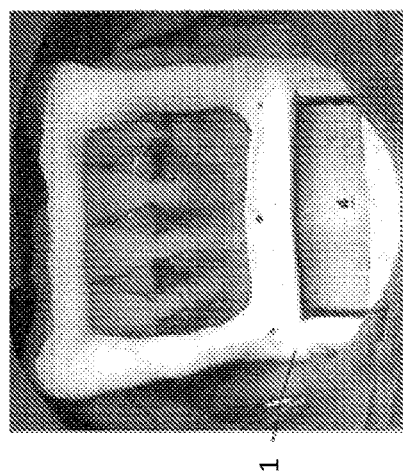

In FIGS. 20*a*-20*c*, a removal of a volume 30 of bone through the guide 1 of FIGS. 19*a*-19*c* is represented. As can be seen, a suitable tool 50 is used rested on the faces of the walls of the guide 1 so as to cut at the perimeter 31 and along the cutting lines L1, L2 the volume of bone 30.

In FIGS. 21*a*-21*c*, a different configuration of guide 1 is represented, also directly rested on the surface 4 of the bone O. Such a guide 1 is assigned to removing a portion of bone at the lateral mandible. FIG. 21*a* shows one of the sections S for delimiting the cutting planes L1 and L2, whereas FIGS. 21*b* and 21*c* show the guide in its entirety in a rendering as rested on the bone surface 4 to delimit the portion 6 of bone to be removed.

The invention claimed is:

1. A method for designing a surgical guide for performing bone harvesting, including:
   providing a three-dimensional image of at least one portion of a bone of a patient where bone harvesting is to be performed, said bone defining an outer surface;
   identifying in said three-dimensional image one or more sensitive anatomic structures to be avoided during said bone harvesting;
   identifying in said three-dimensional image a volume of bone suitable for being removed in said bone harvesting, said volume excluding said sensitive anatomic structures, and said volume being delimited by a portion of said outer surface of said bone defining a perimeter and by a mantle extending from said perimeter inside said bone, said mantle including, for each point of said perimeter, a mantle segment forming a predetermined angle with said portion of said outer surface, said angle corresponding to a cutting direction inside said bone identified in said three-dimensional image;
   and establishing the parameters of said surgical guide, including:
      defining a guide surface suitable for facing said outer surface of said bone, said guide surface comprising a work area delimited by guide walls;
      and angling at least one of said guide walls with respect to said guide surface, so that said guide wall includes a face that constitutes a geometrical extension of a portion of said mantle of said bone volume when said surgical guide faces said portion of outer surface of bone, so that said face includes, for each point of said perimeter of work area, a guide segment forming a predetermined angle with respect to said guide surface, said guide segment extending a length from said guide surface to define a stop surface, said stop surface adapted to contact an aspect of a bone-harvesting tool to set a working depth of the bone-harvesting tool, said working depth being less than a distance along said cutting direction to said one or more sensitive anatomical structures from said guide surface.

2. The method for designing a surgical guide according to claim 1, further including: generating a computer-readable file including said design parameters of said guide.

3. The method for designing a surgical guide according to claim 1, wherein the step of establishing the design parameters of said guide includes:
   defining an upper guide wall, upperly delimiting said portion of surface of said volume of bone to be harvested;
   defining a lower guide wall, lowerly delimiting said portion of surface of said volume of bone to be harvested;
   defining a right side guide wall, delimiting the right hand side of said portion of surface of volume of bone to be harvested;
   defining a left side guide wall, delimiting the left hand side of said portion of surface of said volume of bone to be harvested;
   connecting said guide walls defining said work area;
   and angling an inner face of at least one of said upper guide wall, said lower guide wall, said right side guide wall, said left side guide wall, with respect to said guide surface as an extension of said mantle.

4. The method for designing a surgical guide according to claim 1, including the step of
   determining in said three-dimensional image a minimum safety distance between said sensitive anatomic structures and the volume of bone to be harvested identified in said three-dimensional image; and
   determining the dimensions of said portion of surface of said mantle and the position of said volume of bone so as to maintain a distance between said sensitive anatomic structures and said volume of bone to be harvested identified in said three-dimensional image at a value greater than or equal to said minimum distance.

5. The method for designing a surgical guide according to claim 1, wherein the step of providing a three-dimensional image includes:
   obtaining a copy of at least one of a radiograph, nuclear magnetic resonance, computed axial tomography, or an echograph of said portion of bone of the patient.

6. The method for designing a surgical guide according to claim 1, including the step of angling said face at an angle comprised between 30° and 160° with respect to the guide surface.

7. The method for designing a surgical guide according to claim 1, wherein the step of establishing the parameters of said guide includes the step of providing a guide body in which a window is made, said body comprising a bottom surface that includes said guide surface and said window including said work area.

8. The method for designing a surgical guide according to claim 1, wherein the step of establishing the parameters of said guide includes the step of providing a guide body comprising a bottom surface and one or more side walls, said bottom surface including said work area and said side walls including said guide walls.

9. The method for designing a surgical guide according to claim 1, wherein the step of establishing the parameters of said guide includes the step of providing a guide body comprising a bottom surface and including a channel closed on itself that divides said body into an outer body and an inner body, said bottom surface including said work area and said channel including opposite inner and outer walls, belonging to said inner and outer body, respectively, said outer walls including said guide walls.

10. The method for designing a surgical guide according to claim 1, wherein the step of establishing the parameters of said guide includes:

designing a support for said guide so as to mount a guide made a predetermined distance from said bone surface.

11. The method for designing a surgical guide according to claim 1, including:

angling all of said guide walls by one or more predetermined angles with respect to said guide surface, so as to form a second mantle, which is a geometrical extension of the mantle of said bone volume, extending from said perimeter of said work area, so as to determine, for each wall one or more cutting directions corresponding to one or more cutting directions inside said bone volume to be removed identified in said three-dimensional image.

12. The method for designing a surgical guide according to claim 11, including:

defining a first working depth, given by the depth in said bone of an intersection point or line of said cutting directions.

13. The method for designing a surgical guide according to claim 1, including:

making one or more of said guide walls of said guide with a predetermined thickness with respect to said guide surface so as to define a second working depth.

14. The method for designing a surgical guide according to claim 13, including:

making, in a wall of said guide, an outer face forming an angle with said face, so as to form a stepped abutment element.

15. A non-transitory computer-readable storage medium comprising a software code configured to carry out the method according to claim 1.

16. A system including:

a computer;

and a computer-readable medium containing instructions that, when executed by the computer, ensure that the computer executes the method according to claim 1.

* * * * *